United States Patent
Goette et al.

(10) Patent No.: US 10,699,409 B2
(45) Date of Patent: Jun. 30, 2020

(54) REMOVING GHOST MARKERS FROM A MEASURED SET OF MEDICAL MARKERS

(71) Applicant: Brainlab AG, Munich (DE)

(72) Inventors: Hubert Goette, Munich (DE); Steffen Heinrich, Munich (DE)

(73) Assignee: BRAINLAB AG, Munich (DE)

( * ) Notice: Subject to any disclaimer, the term of this patent is extended or adjusted under 35 U.S.C. 154(b) by 0 days.

(21) Appl. No.: 16/494,109

(22) PCT Filed: Apr. 27, 2017

(86) PCT No.: PCT/EP2017/060098
§ 371 (c)(1),
(2) Date: Sep. 13, 2019

(87) PCT Pub. No.: WO2018/196982
PCT Pub. Date: Nov. 1, 2018

(65) Prior Publication Data
US 2020/0134816 A1      Apr. 30, 2020

(51) Int. Cl.
*G06T 7/00* (2017.01)
*A61B 90/00* (2016.01)

(52) U.S. Cl.
CPC ........ *G06T 7/0012* (2013.01); *A61B 90/361* (2016.02); *A61B 2090/371* (2016.02);
(Continued)

(58) Field of Classification Search
USPC ....................................................... 702/196
See application file for complete search history.

(56) References Cited

U.S. PATENT DOCUMENTS

| 7,519,502 B1* | 4/2009 | Carneal | G01B 11/24 702/167 |
| 9,561,387 B2* | 2/2017 | Yan | A61B 6/03 |
| 2004/0128102 A1* | 7/2004 | Petty | G01S 5/163 702/150 |
| 2005/0059879 A1 | 3/2005 | Sutherland et al. | |

(Continued)

FOREIGN PATENT DOCUMENTS

| EP | 1563799 A1 | 8/2005 |
| JP | 2005168709 A | 6/2005 |

(Continued)

OTHER PUBLICATIONS

Holzreiter et al, "Autolabeling 3D tracks using neural networks", Jan. 1, 2005 (Jan. 1, 2005), vol. 20, No. 1, p. 1-8.

(Continued)

*Primary Examiner* — Paul D Lee
(74) *Attorney, Agent, or Firm* — Middleton Reutlinger

(57) ABSTRACT

A method for removing ghost markers from a measured set of medical markers, wherein the measured set of markers represents the positions of real markers and the positions of ghost markers, comprising the steps of: —calculating all possible minimal marker sets, wherein a minimal marker set is a subset of the measured set and a minimal marker set consists of the smallest possible number of markers which would cause the measured set to be measured; —calculating the smallest extent of each minimal marker set, wherein the smallest extent is the smallest extent among the extents in three orthogonal directions; and —selecting the minimal marker set having the smallest out of the smallest extents as a marker set without ghost markers.

15 Claims, 10 Drawing Sheets

(52) U.S. Cl.
CPC ... *A61B 2090/373* (2016.02); *A61B 2090/376* (2016.02); *A61B 2090/3937* (2016.02); *A61B 2090/3966* (2016.02); *A61B 2090/3983* (2016.02); *G06T 2207/10012* (2013.01); *G06T 2207/30208* (2013.01)

(56) References Cited

U.S. PATENT DOCUMENTS

| | | | |
|---|---|---|---|
| 2008/0285854 A1* | 11/2008 | Kotake | G06T 7/73 382/190 |
| 2010/0331855 A1* | 12/2010 | Zhao | A61B 34/30 606/130 |

FOREIGN PATENT DOCUMENTS

| | | |
|---|---|---|
| WO | WO2016108720 A1 | 7/2016 |
| WO | WO2018196982 A1 | 1/2018 |

OTHER PUBLICATIONS

Northern Digital Inc., "Passive Polaris Spectra User Guide" 2008; 124 Pages.

Yan et al., "Ghost Marker detection and elimination in marker-based optical tracking systems for real-time tracking in stereotactic body radiotherapy" https://www.ncbi.nlm.nih.gov/pubmed/25281952 Abstract only, 2014 (Accessed Sep. 13, 2019) 2 Pages.

Stroian et al., "Elimination of ghost markers during dual sensor-based infrared tracking of multiple individual reflective markers" https://www.ncbi.nlm.nih.gov/pubmed/15305453 Abstract only, 2004 (Accessed Sep. 13, 2019) 2 Pages.

International Search Report and Written Opinion issued in Application No. PCT/EP2017/060098 dated Apr. 27, 2017; 9 Pages.

* cited by examiner

REMOVING GHOST MARKERS FROM A MEASURED SET OF MEDICAL MARKERS

TECHNICAL FIELD

The present invention relates to a computer implemented method for removing ghost markers from a measured set of markers and to a corresponding computer program and system.

SUMMARY

Tracking objects, such as bones, other parts of a patient or objects like medical instruments is an essential part in many modern medical procedures. In a typical approach, a set of markers is attached to the object to be tracked and detected using a stereoscopic detection system. The markers can be visual markers in the visual spectrum or x-ray markers which significantly dampen or completely block x-ray radiation. Optical markers can be reflective or active, that is light emitting.

A stereoscopic detector typically comprises two or more two-dimensional imaging units which create two-dimensional images depicting one or more markers. For each pixel in a two-dimensional image, a line in space, which is mapped onto this pixel, is known due to the structure of the imaging unit. In addition, the relative positions between the imaging units are known. The lines in space on which a particular marker lies intersect each other at the spatial location of the marker, such that the spatial location of the marker can be determined from the pixels in the two-dimensional images of the imaging units which show this marker by triangulation.

It is possible to find a marker in a two-dimensional image, but typically not to determine the identity of a marker. This means that a set of markers can be found in each of two images, but it is not evident which marker in one set corresponds to a marker in the other set. So there are two sets of lines in space, one set for each set of found markers. A marker only exists in space where two lines, one from each set of lines, intersect. But depending on the geometry of the markers and the viewing directions of the cameras, there might be intersections of lines belonging to different markers. So if the lines in space corresponding to different markers in different two-dimensional images also intersect, an additional marker is detected at the spatial position of the intersection, even if there is no real marker at this spatial location. This additional marker is called a ghost marker.

A measured set of medical markers therefore represents the positions of real (existing) markers and positions of ghost markers, which are artifacts caused by the effects mentioned above.

Ghost markers can easily be eliminated from a measured set of medical markers if the relative position between the markers is known or when their positions are defined beforehand in a coordinate system geometrically linked to the marker. This is the case for a predefined and rigid marker device. Measured markers not corresponding to the real geometry of the marker device can be discarded.

However, there is a problem if the geometry of the marker device is unknown or variable. In this case, ghost markers cannot be eliminated in the same way as for rigid marker devices. The present invention therefore aims at enabling and/or improving the removal of ghost markers from a measured set of medical markers even if the marker configuration is variable and/or unknown.

The method, the program and the system are defined by the appended independent claims. Advantages, advantageous features, advantageous embodiments and advantageous aspects of the present invention are disclosed in the following and contained in the subject-matter of the dependent claims. Different advantageous features can be combined in accordance with the invention wherever technically expedient and feasible. Specifically, a feature of one embodiment which has the same or a similar function to another feature of another embodiment can be exchanged with said other feature, and a feature of one embodiment which adds an additional function to another embodiment can in particular be added to said other embodiment.

The present invention relates to a method for removing ghost markers from a measured set of medical markers, wherein the measured set of markers represents the positions of real markers and the positions of ghost markers.

In one aspect, the method comprises the steps of calculating all possible minimal marker sets, wherein a minimal marker set is a subset of the measured set and a minimal marker set consists of the smallest possible number of markers which would cause the measured set to be measured, calculating the smallest extent of each minimal marker set, wherein the smallest extent is the smallest extent among the extents in three orthogonal directions, and selecting the minimal marker set having the smallest out of the smallest extents as a marker set without ghost markers.

As explained above, a ghost marker is an additional, virtual marker which is caused by the constellation of the real markers and their spatial locations relative to the imaging units. However, it is not possible to immediately decide which markers in the measured set are real markers and which are ghost markers, respectively. The first step therefore determines all possible minimal marker sets, which can be understood as real marker candidate sets. A real marker candidate set is a marker set which might represent only real markers. If those markers were the real markers, they would create ghost markers such that the measured set would be measured or established. In a simple example, a first pair of markers, being the real markers, creates a second pair of markers, which are ghost markers, such that the measured set of medical markers comprises four markers. There are then two possible minimal marker sets, one comprising the first marker pair and one comprising the second marker pair. The reason for this is that, if the ghost markers were the real markers, they would also cause artifacts at the locations of the real markers.

Minimal marker sets can be calculated easily and unambiguously due to the nature of ghost markers. A minimal marker set typically is a set in which there is exactly one marker on every line of all imaging units. However, there can be more than one marker on a line if the numbers of lines of the imaging units are different, which implies that there are two or more real markers on the same line.

A minimal marker set would produce such a ghost marker set, that the combined set of the minimal marker set and the ghost marker set equals the measured set.

Once all possible minimal marker sets have been calculated, there must be one among those minimal marker sets which only represents the positions of real markers. This minimal marker set has to be identified next.

A first step of this identification is calculating the smallest extent of each minimal marker set. The extent means the geometric "size" or length of the marker set in a particular direction. Each minimal marker set represents the locations of the markers comprised therein. The smallest extent is the geometric size in the direction in which the minimal marker set is the flattest. In this document, the expression geometric size thus refers to the volume occupied by the markers as represented by a marker set. In other words, the smallest extent of a minimal marker set is the length of the shortest edge of a rectangular bounding box around the minimal marker set.

For a particular minimal marker set, an infinite number of rectangular cuboids, which are rectangular bounding boxes for the minimal marker set, can be determined. Each of those rectangular cuboids has three extents in the three orthogonal directions of the edges of the rectangular cuboid, wherein the three extents depend on the alignment of the cuboid relative to the markers. In one embodiment, the rectangular cuboid for which the smallest of those three extents, that is the shortest edge, is minimized is detected as the minimum bounding box and this minimized extent is assigned to the minimal marker set.

In other words, the three orthogonal directions are those directions, relative to the markers of the minimal marker set, for which the smallest extent of the minimal marker set is minimized over all possible alignments of the three orthogonal directions relative to the minimal marker set.

Expressed differently, the smallest extent of a minimal marker set is the size in a direction in which the minimal marker set is the flattest.

Then the minimal marker set having the smallest out of the smallest extents is selected as a marker set without ghost markers. In other words, the flattest of all minimal marker sets is selected.

Briefly summarizing the above aspect, all smallest possible subsets of the measured set which would create ghost markers such that the measured set would result are determined and the flattest out of those sets is assumed as the marker set without ghost markers.

The present invention works best for flat marker configurations. Those configurations are typical for markers which are arranged on a flexible flat object, such as a fabric, which can optionally adapt its shape to the surface of an object such as a patient. The markers are then widely distributed in two out of three orthogonal directions, but only little in the third out of the three orthogonal directions, such that the marker configuration is basically flat or near-flat.

In one embodiment, the step of calculating the smallest extent involves calculating the principal axes of the minimal marker set and using the directions of the principal axes as the three orthogonal directions. The positions of the markers in a minimal marker set can be understood as a random variable having three dimensions. By use of principal component analysis, the covariances of the xyz-coordinates of the marker positions in the minimal marker set become zero while their variances are being maximized and the eigenvectors given by the principal components analysis give the principal axes which can be used as the three orthogonal directions in x, y, and z.

In one embodiment, the principal axes correspond to eigenvectors of a covariance matrix of the positions of the markers in the measured set in a measurement coordinate system. The measurement coordinate system is typically a reference system of the stereoscopic detection system.

The calculation can be performed as follows:

The random variable v has 3 dimensions x, y, z and describes the coordinates of the n markers comprised in the minimal marker set in the camera's measurement coordinate system:

$$v=(x,y,z)^T$$

The random variable v' has 3 dimensions x', y', z' and describes the coordinates of the markers in the principal axes coordinate system to be calculated:

$$v'=(x',y',z')^T$$

The variance of a random variable x is defined as var(x), analog for y and z:

$$\mathrm{var}(x) = \sum_{i=1}^{n} \frac{(X_i - \bar{x})^2}{n-1}$$

The covariance of two random variables x and y is defined as cov(x,y), analog for cov(y,z) and cov(x,z):

$$\mathrm{cov}(x, y) = \sum_{i=1}^{n} \frac{(X_i - \bar{x})(Y_i - \bar{y})}{n-1}$$

The covariance matrix C has as its elements the variances and covariances of the random variables x, y, z:

$$C = \begin{pmatrix} \mathrm{var}(x) & \mathrm{cov}(x, y) & \mathrm{cov}(x, z) \\ \mathrm{cov}(y, x) & \mathrm{var}(y) & \mathrm{cov}(y, z) \\ \mathrm{cov}(z, x) & \mathrm{cov}(z, y) & \mathrm{var}(z) \end{pmatrix}$$

With x, y, z representing the three dimensions of the random variable v, C becomes the covariance matrix of v:

$$C=\mathrm{Cov}(v)$$

A known property of covariance matrices when multiplied by a matrix A is:

$$\mathrm{Cov}(Av)=A*\mathrm{Cov}(v)*A^T$$

This is the same for v':

$$\mathrm{Cov}(Av')=A*\mathrm{Cov}(v')*A^T$$

Substituting v by Av' leads to:

$$\mathrm{Cov}(v)=A*\mathrm{Cov}(v')*A^T$$

This rotation will yield a coordinate system, where the locations formerly represented by v are represented by v'.

Since the coordinate system shall be aligned with the principal axes, the covariance elements of Cov(v') must all be 0. Thus Cov(v') shall become a diagonal matrix:

$$D=\mathrm{Cov}(v')$$

That leads to following equation to be solved for A and D:

$$C=\mathrm{Cov}(v)=A*D*A^T$$

In the present case, A is a rotation matrix and is orthogonal, such that $A^T=A^{-1}$, and the equation to be solved simplifies to the known problem of the diagonalization of a symmetrical matrix C:

$$C=A*D*A^{-1}$$

D becomes the covariance matrix of v'. It has only diagonal elements greater than zero. They represent the variances of x', y', z'. All covariance elements are zero. The found rotation matrix A transforms the locations of the markers from the system of the principal axes to the measurement system:

$$Av'=v$$

The eigenvectors $ev_i$ describe the axes x', y', z' respectively as vectors in the measurement system x, y, z.

$$A=(ev_1,ev_2,ev_3)$$

The eigenvalues $\lambda_i$ measure the geometrical extent of the marker set along the respective axis $ev_i$.

$$D=\text{diag}(\lambda_1,\lambda_2,\lambda_3)$$

Therefore, in one embodiment, the eigenvalues of the covariance matrix are calculated and the smallest extent is calculated on the basis of at least one of the eigenvalues.

In one example, the smallest eigenvalue of each minimal marker set is used as the smallest extent of the minimal marker set.

In another example, the product of the eigenvalues is calculated for each minimal marker set and this product is used as the smallest extent.

In another example, the smallest eigenvalue is divided by the product of the two other eigenvalues and the result of this division is used as the smallest extent.

In another embodiment, a bounding box, and preferably a minimal bounding box, around all markers is calculated for every minimal marker set and the minimal marker set having the bounding box with the smallest volume is selected.

In another embodiment, the sum of all distances (or powers thereof) between each marker in a minimal marker set and a reference point are summed up and the minimal marker set with the smallest sum is selected. The reference point is for example the center of the minimal marker set.

In this document, a reference to a marker set can also mean a reference to the markers within this marker set. So the geometric size of the marker set means the size of the volume occupied by the markers in the marker set and the center of the marker set means the geometric center of the locations of the markers in the marker set.

In the three subsequent exemplary embodiments, it is assumed that the measured set of medical markers is measured using two cameras. However, they can equally be applied for more than two cameras. The expression "camera" means any imaging unit which can capture a two-dimensional image showing one or more markers, and can thus also be an x-ray detector, for example. In one exemplary embodiment, calculating the minimal marker set involves the step of acquiring a first line set for the first camera and a second line set for the second camera, wherein each line set consists of a set of straight lines in space, each straight line runs through the front lens of the corresponding camera and at least one real marker lies on a straight line. A straight line is a line in space such that all markers lying on this straight line are imaged by the camera at the same pixel position in the two-dimensional image. A straight line can thus also be referred to as a line of sight of a camera. In this document, the expression "front lens" means the part of the camera at which the electromagnetic or x-ray radiation to be detected enters the camera. A particular pixel in the two-dimensional image generated by the camera corresponds to a particular straight line as defined by the structure of the camera.

This first step obtains those lines in space on which at least one marker lies. However, a ghost marker can only occur if two straight lines of one line set each intersect with at least two straight lines of the other line set.

Another step is therefore finding a ghost marker susceptible line set, wherein a ghost marker susceptible line set comprises all lines of the first and second line sets which lie in the same plane and each of those lines intersects with at least two lines of the respective other line set in the ghost marker susceptible line set, and comprises at least two lines of each line set.

As explained above, a marker is detected at a location at which a line corresponding to the first camera and a line corresponding to the second camera intersect. If one line corresponding to one camera intersects two lines corresponding to the other camera, then two markers are detected. Those two markers are real markers. However, if two lines corresponding to one camera each intersect two lines corresponding to the other camera, then there are four points of intersection, but not necessarily four, but at least two real markers at those points of intersection. For geometric reasons, all those lines must lie in the same plane, because the quadruple intersection would not be possible otherwise. The aforementioned applies equally for more than two lines corresponding to one camera intersecting two (or more) lines corresponding to the other camera.

Calculating the minimal marker set further involves the step of determining the minimal marker sets as those marker sets for which each line in the line set having more lines in the ghost marker susceptible line set than the other line set intersects exactly one line in the other line set and there is at least one marker on each line of the other line set. If the number of lines of the first line set and the second line set in the ghost marker susceptible line set is equal, then the minimal marker sets are those marker sets for which each line of one line set intersects exactly one line of the other line set and there is exactly one marker on each line.

In one example, determining a minimal marker set starts with a minimal marker set comprising all markers on those lines of the first line set which intersect with exactly one line of the second line set, which means markers being unambiguously detectable as real markers. Then one line of the first line set comprised in the ghost marker susceptible line set is selected and a line of the second line set comprised in the ghost marker susceptible line set is selected and a marker at the intersection of those lines is added to the minimal marker set. The two selected lines are then removed from the ghost marker susceptible line set and the process is repeated until there are no more intersecting lines in the ghost marker susceptible line set.

If the numbers of lines of the two line sets in the original ghost marker susceptible line set are not identical, there remain lines of one of the line sets, which is referred to as the larger line set, in the ghost marker susceptible line set. In this case, a remaining line of the larger line set is selected, a point of intersection with a line of the other line set as originally comprised in the ghost marker susceptible line set is calculated, a marker at the intersection is added to the minimal marker set and the selected remaining line is removed from the ghost marker susceptible line set. In this context, the expression "as originally comprised in the ghost marker susceptible line set" means the state of the ghost marker susceptible line set before a line was removed therefrom.

The approach described above is used repeatedly to determine all possible minimal marker sets by determining all possible permutations of intersections.

The approach described so far covers all markers in a particular plane. However, there might be other planes in which markers lie such that ghost markers are possible. The step of finding a ghost marker susceptible line set is therefore repeated for another plane and minimal marker sets are determined for this plane. Calculating all possible minimal marker sets then involves finding all combinations of the minimal marker sets corresponding to a first plane with the minimal marker sets corresponding to the second plane.

In another exemplary embodiment, calculating the minimal marker sets involves the step of acquiring, from the stereoscopic camera, a marker matrix assigning each marker in the measured set to a corresponding line in a first line set for the first camera and a corresponding line in a second line set for the second camera, wherein each line set consists of a set of straight lines in space, each straight line runs through the front lens of the corresponding camera and at least one real marker lies on a straight line. Regarding the nature of the camera, the meaning of the front lens and the definition of the straight lines, the same applies as in the first exemplary embodiment above.

The present exemplary embodiment is particularly suitable in cases in which the stereoscopic camera provides the marker matrix as an output.

The marker matrix represents knowledge about intersections of lines in the first line set with lines in the second line set, because if a marker is assigned to a line of the first line set and a line of the second line set, this implies that those two lines intersect. In the marker matrix, a marker is typically assigned to exactly one line of the first line set and to one line of the second line set.

Calculating the minimal marker set further involves the step of finding all sub-matrices of the marker matrix in which every line belonging to the larger line set has exactly one marker assigned thereto. The lines of the other line set each have at least one marker assigned, wherein each assigned marker corresponds to a marker assigned to the lines in the larger line set. In this document, the larger line set is the line set having more lines therein. If both line sets have the same number of lines, then the larger line set can be any of the line sets and each line has exactly one marker assigned thereto.

In an exemplary implementation, the process thins out copies of the marker matrix. It iterates through all lines of the larger line set. If only one marker is assigned to the selected line, the corresponding entry in the marker matrix is maintained. If more than one marker is assigned to the selected line, one of those assigned markers is selected and the other marker entries assigned to the selected line are removed from the matrix. The line in the other line set which has the selected marker assigned thereto is selected. Then deletable markers in the selected line of the other line set are determined. Those deletable markers are all markers in the line which are not assigned to lines of the larger line set which have not been selected yet and are not selected markers in previously selected lines of the larger line set. The matrix entries on the selected line of the other line set and corresponding to deletable markers are deleted from the marker matrix. If the process has not yet iterated through all lines of the larger line set, the next iteration starts.

Once all iterations are completed, invalid marker entries are deleted from the marker matrix. Invalid marker entries are superfluous entries belonging to the other line set and indicate markers not selected for any of the lines of the larger line set.

The process is repeated with a new copy of the marker matrix until all such sub-matrices are found. This means finding all possible permutations of entries in the marker matrix as explained above.

If both line sets comprise the same number of lines, the above process results in sub-matrices in which every line has exactly one marker assigned thereto. If the numbers of lines in the two line sets are different, the above process results in sub-matrices in which each line of the larger line set has exactly one marker assigned thereto and each line of the other (smaller) line set has at least one marker assigned thereto.

However, in the case of different numbers of lines in the two line sets, there may be sub-matrices which are invalid because not all lines of the smaller line set have markers assigned thereto in the sub-matrix. Those sub-matrices in which at least one line of the smaller line set has no marker assigned thereto are discarded.

Calculating the minimal marker sets then further involves the step of determining the minimal marker sets from the sub-matrices. In particular, the spatial locations corresponding to the entries in a sub-matrix constitute a minimal marker set.

In still another exemplary embodiment, the measured set of medical markers is measured using a stereoscopic camera comprising two cameras and calculating the minimal marker sets involves the step of acquiring, from the stereoscopic camera, a marker matrix assigning each marker in the measured set to one line in a first line set for the first camera and to one line in a second line set for the second camera, wherein each line set consists of a set of straight lines in space, each straight line runs through the front lens of the corresponding camera and at least one real marker lies on a straight line. This is the same as in the preceding exemplary embodiment.

Calculating the minimal marker sets further involves finding all sub-matrices of the marker matrix which fulfill two rules. The first rule is that every line of the first line set and every line of the second line set has exactly one marker assigned thereto. The second rule is that every marker in the sub-matrix is assigned to exactly one line of the first line set and to exactly one line of the second line set.

Calculating the minimal marker sets then further involves the step of determining the minimal marker sets from the sub-matrices. In particular, the spatial locations corresponding to the entries in a sub-matrix constitute a minimal marker set This exemplary embodiment is suitable if the first and second line sets comprise the same numbers of lines.

An exemplary implementation for finding the sub-matrices will now be explained with reference to the subsequent pseudocode.

```
set ActiveRowsLeft to the number of lines in the line set of one of the cameras (first line set)
set ActiveRowsRight to the number of lines in the line set of the other camera (second line set)
quit if ActiveRowsLeft <> ActiveRowsRight
set MarkerSize to the number of markers in the marker matrix
set MarkerSizeLimit to (2^MarkerSize) − 1
loop 1: count MarkerMask from 1 to MarkerSizeLimit
{
    count number of bits == in binary representation of MarkerMask
    continue with next iteration of loop 1 if number of bits <> ActiveRowsLeft
```

```
    set MarkersFoundLeft to 0
    set MarkersFoundRight to 0
    loop 2: count LineNumber from 1 to ActiveRowsLeft
    {
        set LeftCameraRow as binary representation of markers comprised in
        LineNumber^th line in the first line set
        set LeftCameraRowResult to result of bit-wise AND combinbation of
        MarkerMask and LeftCameraRow
        count number of bits == 1 in LeftCameraRowResult
        continue with next iteration of loop 1 if number of bits >1
        set RightCameraRow as binary representation of markers comprised in
        LineNumber^th line in the second line set
        set RightCameraRowResult to result of bit-wise AND combination of
        MarkerMask and RightCameraRow
        count number of bits == 1 in RightCameraRowResult
        continue with next iteration of loop 1 if number of bits >1
        perform binary OR combination of MarkersFoundLeft with
        LeftCameraRowResult
        perform binary OR combination of MarkersFoundRight with
        RightCameraRowResult
    } end loop 2
    set MarkersFound to result of bit-wise AND combination of MarkersFoundLeft
    and MarkersFoundRight
    count number of bits == 1 MarkersFound
    MarkerMask represents minimal marker set if number of bits = ActiveRowsLeft
} end loop 1
```

In steps 1 and 2, the numbers of lines in the two line sets are determined. The words "left" and "right" are only used to distinguish between the two cameras, which are typically side by side. However, they could also by on top of each other or arranged otherwise. In one example, the numbers of lines equal 3. If they are not equal, the code stops at step 3. In step 4, MarkerSize is set to the number of markers in the marker matrix. In the example, this number is 5.

MarkerSizeLimit in step 5 is set such that the number of digits or bits in its binary representation equals MarkerSize, which is 5 in the example. Loop1 starting in step 6 then counts MarkerMask from 1 to MarkersizeLimit. MarkerMask thus iterates through all permutations of up to five markers, but at least one marker. A "1" means that the corresponding marker is present, while a "0" means that the corresponding marker is not present. Each permutation is then tested whether or not it represents a minimal marker set. It is therefore also referred to as candidate marker set.

The number of markers in a minimal marker set is ActiveRowsLeft, such that steps 8 and 9 proceed to the next permutation if the number of markers in the current permutation does not equal ActiveRowsLeft.

In steps 10 and 11, MarkersFoundLeft and MarkersFoundRight are initialized. Those variables, in their binary form, will later represent the markers of the current permutation which are assigned to at least one line of the first line set and the second line set, respectively.

The loop2 starting in step 12 iterates through all lines of both line sets. In the example, it iterates through the three lines of the first line set and the second line set. In step 14, LeftCameraRow is set as a binary representation of the markers lying on the current line corresponding to the current iteration in the first line set. If a marker is present in the line, then the corresponding bit is set to "1", otherwise to "0". In the example, LeftCameraRow has 5 bits.

In step 15, a LeftCameraRowResult is set to be the result of a bit-wise AND combination of MarkerMask and LeftCameraRow. This means a binary, or bit-wise, multiplication of those variables. The n-th bit of LeftCameraRowResult is 1 if both the n-th bit of MarkerMask and the n-th bit of LeftCameraRow are 1, otherwise it is 0. The result is a binary number, wherein each bit indicates whether or not the corresponding marker of the candidate marker set lies on the current line.

In step 16, the number of bits having the value "1" in LeftCameraRowResult is counted. If this number does not equal 1, then the code proceeds to the next permutation of loop1. The rules mentioned above state that there must be exactly one marker on each line. This is verified in steps 14 to 18 for the first line set.

Steps 18 to 22 are the same as steps 14 to 18, but for the second line set instead of the first line set.

In step 22, MarkersFoundLeft is binary OR combined with LeftCameraRowResult. This means that the bit having the value "1" in LeftCameraRowResult is also set in MarkersFoundLeft. In other words, the marker indicated in LeftCameraRowResult is added to a list for the first line set, the list comprising those markers of the candidate marker set which were identified in the iterations of loop2 performed so far. The same happens in step 23 for the second line set.

In step 24, loop2 ends. In step 25, MarkersFound is set to be the result of a bit-wise AND combination of MarkersFoundLeft and MarkersFoundRight. This means a binary multiplication of MarkersFoundLeft and MarkersFoundRight. The result is a binary number which indicates the markers in both MarkersFoundLeft and MarkersFoundRight. In the example, MarkersFound has 5 bits. The lists obtained in steps 22 and 23 must be consistent, which means that they must comprise the same markers. So the lists are merged in step 25.

In step 26, the number of bits in MarkersFound is counted. This number is the number of markers in the candidate marker set. If this number equals ActiveRowsLeft, then MarkerMask represents a minimal marker set as determined in step 27. A marker set corresponding to Marker Mask is then added to the set of minimal marker sets.

In all variables MarkerMask, MarkersFoundLeft, MarkersFoundRight, LeftCameraRow, RightCameraRow, LeftCameraRowResult, RightCameraRowResult and MarkersFound, the same bit always represents the same marker of the measured set of markers.

In one aspect of the invention, the measured set of medical markers was obtained by use of a stereoscopic camera using two cameras, wherein a camera could also be an X-ray camera as described above. The method for removing ghost markers from the measured set of medical markers comprises the steps of finding a potential ghost marker subset of the measured set, the potential ghost marker subset comprising real markers and ghost markers caused by the real markers, calculating the distance of each marker in the potential ghost marker subset to the stereoscopic camera, removing the marker with the smallest distance and the marker with the largest distance from the measured set and the potential ghost marker subset and repeating the removing step if the potential ghost marker subset comprises further potential ghost markers.

The potential ghost marker subset is a subset of the measured set, wherein all markers in the measured set which cannot be ghost markers, are not comprised in the potential ghost marker subset. In addition, the ghost marker subset preferably only comprises markers having spatial locations in the same plane in 3D space. This means that any marker in the potential ghost marker subset might be a ghost marker caused by two other markers in the potential ghost marker subset. The potential ghost marker subset is then analyzed in order to identify ghost markers to be removed from the measured set of medical markers.

The elimination of ghost markers from the potential ghost marker subset is based on the distances of the markers comprised in the potential ghost marker subset to the stereoscopic camera, for example to a common reference point defined with respect to the stereoscopic camera. In particular, the marker with the smallest distance and the marker with the largest distance are found in the potential ghost marker subset and are then removed both from the measured set and the potential ghost marker subset. This works particularly well for specific configurations of the markers, such as a flat arrangement of the markers. This means that the markers are spread relatively widely over two orthogonal directions, but hardly over a third orthogonal direction.

The approach keeps removing the marker with the smallest distance and the marker with the largest distance until there is no further potential ghost marker in the potential ghost marker subset.

In one embodiment, the distance between a marker and the stereoscopic camera is the distance between the marker and the middle of a straight line which connects the two cameras, for example the centers, the image sensors or the front lenses of the two cameras.

In one embodiment, the steps of finding a potential ghost marker subset, calculating the distances, removing the markers and repeating the removing step are repeated for another potential ghost marker set, for example for a potential ghost marker set comprising markers lying in a different plane in 3D space than the markers in (a) previous potential ghost marker set(s). With this iterative approach, ghost markers lying in different planes in space are removed plane by plane.

The step of finding a potential ghost marker subset of the measured set involves the step of acquiring a first line set for the first camera and a second line set for the second camera, wherein each line set consists of a set of straight lines in space, each straight line runs through the front lens of the corresponding camera and at least one real marker lies on a straight line. Regarding the expressions "front lens", "camera" and "straight line", the same applies as explained above regarding the other aspect of the invention.

It further comprises finding a ghost marker susceptible line set, wherein a ghost marker susceptible line set comprises all lines of the first and second line sets which lie in the same plane and each of those lines intersects at least two lines of the respective other line set in the ghost marker susceptible line set and comprises at least two lines of each line set. The steps of acquiring the line sets and finding a ghost marker susceptible line set are the same as explained above with respect to an embodiment of the other aspect of the invention and are therefore not explained in detail again.

The step of finding a potential ghost marker subset further involves the step of adding all markers of the measured set to the potential ghost marker subset that lie on an intersection of two lines of the ghost marker susceptible line set, wherein one of those two lines is from the first line set and the other of those two lines is from the second line set.

Each line in the first line set and the second line set is a line in space on which a real marker lies. However, if two lines of one line set intersect with two lines of the other line set, this can be caused by different constellations. In one constellation, there are only two real markers at two intersections, which means that ghost markers are detected at the other intersections. In another case, there are real markers at all intersections, such that there are no ghost markers detected on the line. However, this case is very unlikely. In addition, there might be real markers at some, but not all intersections, such that ghost markers are detected at all other intersections.

In another embodiment, a marker matrix as explained above is used for finding a potential ghost marker subset of the measured set. In one implementation, the marker matrix is analyzed for all lines of one of the two line sets. If more than one marker is assigned to a line, then all markers assigned to this line are added to the potential ghost marker subset. The resulting potential ghost marker subset is also referred to as the initial potential ghost marker subset. In a next step, all markers in the potential ghost marker subset which do not lie in the same plane are removed from the potential ghost marker subset. Starting from the initial potential ghost marker subset, this removal might be performed again for another plane in order to determine another potential ghost marker subset.

As described above, the marker with the smallest distance and the marker with the largest distance are removed from the measured set and the potential ghost marker subset until the potential ghost marker subset comprises no further potential ghost markers. This can be verified in a plurality of ways.

In one example, a threshold value is determined. The threshold value is for example the larger one of the number of lines out of the first line set in the ghost marker susceptible line set and the number of lines out of the second line set in the ghost marker susceptible line set. In another embodiment, the threshold value is the larger one of the number of lines of the first line set and the number of lines of the second line set which each have more than one marker assigned in the marker matrix. The removing step is then repeated until the remaining number of markers in the potential ghost marker subset is equal to or less than the threshold value.

In another embodiment, the removing step is repeated until the potential ghost marker subset comprises only markers such that there is exactly one marker on each line of the ghost marker susceptible line set or the lines represented by the marker matrix.

The present invention further relates to a program which, when running on a computer, causes the computer to perform the method as explained herein. It further relates to a program storage medium on which the program is stored, in particular in a non-transitory form.

The invention further relates to a computer on which the aforementioned program is stored and/or run.

As mentioned above, the invention works best if the configuration of the markers is flat or near-flat, in particular in its appearance to the stereoscopic detection system.

One possible test whether or not the marker configuration is (sufficiently) flat is as follows. Each marker forms a triangle with the detectors in the stereoscopic detection system, for example with the front lenses of two cameras. The marker configuration is (sufficiently) flat if there is no other marker in each of the triangles.

DEFINITIONS

The method in accordance with the invention is for example a computer implemented method. For example, all the steps or merely some of the steps (i.e. less than the total number of steps) of the method in accordance with the invention can be executed by a computer (for example, at least one computer). An embodiment of the computer implemented method is a use of the computer for performing a data processing method. An embodiment of the computer implemented method is a method concerning the operation of the computer such that the computer is operated to perform one, more or all steps of the method.

The computer for example comprises at least one processor and for example at least one memory in order to (technically) process the data, for example electronically and/or optically. The processor being for example made of a substance or composition which is a semiconductor, for example at least partly n- and/or p-doped semiconductor, for example at least one of II-, III-, IV-, V-, VI-semiconductor material, for example (doped) silicon and/or gallium arsenide. The calculating steps described are for example performed by a computer. Determining steps or calculating steps are for example steps of determining data within the framework of the technical method, for example within the framework of a program. A computer is for example any kind of data processing device, for example electronic data processing device. A computer can be a device which is generally thought of as such, for example desktop PCs, notebooks, netbooks, etc., but can also be any programmable apparatus, such as for example a mobile phone or an embedded processor. A computer can for example comprise a system (network) of "sub-computers", wherein each sub-computer represents a computer in its own right. The term "computer" includes a cloud computer, for example a cloud server. The term "cloud computer" includes a cloud computer system which for example comprises a system of at least one cloud computer and for example a plurality of operatively interconnected cloud computers such as a server farm. Such a cloud computer is preferably connected to a wide area network such as the world wide web (WWW) and located in a so-called cloud of computers which are all connected to the world wide web. Such an infrastructure is used for "cloud computing", which describes computation, software, data access and storage services which do not require the end user to know the physical location and/or configuration of the computer delivering a specific service. For example, the term "cloud" is used in this respect as a metaphor for the Internet (world wide web). For example, the cloud provides computing infrastructure as a service (IaaS). The cloud computer can function as a virtual host for an operating system and/or data processing application which is used to execute the method of the invention. The cloud computer is for example an elastic compute cloud (EC2) as provided by Amazon Web Services™. A computer for example comprises interfaces in order to receive or output data and/or perform an analogue-to-digital conversion. The data are for example data which represent physical properties and/or which are generated from technical signals. The technical signals are for example generated by means of (technical) detection devices (such as for example devices for detecting marker devices) and/or (technical) analytical devices (such as for example devices for performing (medical) imaging methods), wherein the technical signals are for example electrical or optical signals. The technical signals for example represent the data received or outputted by the computer. The computer is preferably operatively coupled to a display device which allows information outputted by the computer to be displayed, for example to a user. One example of a display device is an augmented reality device (also referred to as augmented reality glasses) which can be used as "goggles" for navigating. A specific example of such augmented reality glasses is Google Glass (a trademark of Google, Inc.). An augmented reality device can be used both to input information into the computer by user interaction and to display information outputted by the computer. Another example of a display device would be a standard computer monitor comprising for example a liquid crystal display operatively coupled to the computer for receiving display control data from the computer for generating signals used to display image information content on the display device. A specific embodiment of such a computer monitor is a digital lightbox. The monitor may also be the monitor of a portable, for example handheld, device such as a smart phone or personal digital assistant or digital media player.

The expression "acquiring data" for example encompasses (within the framework of a computer implemented method) the scenario in which the data are determined by the computer implemented method or program. Determining data for example encompasses measuring physical quantities and transforming the measured values into data, for example digital data, and/or computing the data by means of a computer and for example within the framework of the method in accordance with the invention. The meaning of "acquiring data" also for example encompasses the scenario in which the data are received or retrieved by the computer implemented method or program, for example from another program, a previous method step or a data storage medium, for example for further processing by the computer implemented method or program. Generation of the data to be acquired may but need not be part of the method in accordance with the invention. The expression "acquiring data" can therefore also for example mean waiting to receive data and/or receiving the data. The received data can for example be inputted via an interface. The expression "acquiring data" can also mean that the computer implemented method or program performs steps in order to (actively) receive or retrieve the data from a data source, for instance a data storage medium (such as for example a ROM, RAM, database, hard drive, etc.), or via the interface (for instance, from another computer or a network). The data acquired by the disclosed method or device, respectively, may be acquired from a database located in a data storage device which is operably to a computer for data transfer between the database and the computer, for example from the database to the computer. The computer acquires the data for use as an input for steps of determining data. The determined data can be output again to the same or another database to be stored for later use. The database or database used for implementing the disclosed method can be located on network data storage device or a network server (for example, a cloud data storage device or a cloud server) or a local data storage device (such as a mass storage device operably connected to at least one computer executing the disclosed method). The data can be made "ready for use" by performing an additional step before the acquiring step. In accordance with this additional step, the data are generated in order to be acquired. The data are for example detected or captured (for example by an analytical device). Alternatively or additionally, the data are inputted in accordance with the additional step, for instance via interfaces. The data generated can for example be inputted (for instance into the computer). In accordance with the additional step (which precedes the acquiring step), the data can also be provided by performing the additional step of storing the data in a data storage medium (such as for example a ROM, RAM, CD and/or hard drive), such that they are ready for use within the framework of the method or program in accordance with the invention. The step of "acquiring data" can therefore also involve commanding a device to obtain and/or provide the data to be acquired. In particular, the acquiring step does not involve an invasive step which would represent a substantial physical interference with the body, requiring professional medical expertise to be carried out and entailing a substantial health risk even when carried out with the required professional care and expertise. In particular, the step of acquiring data, for example determining data, does not involve a surgical step and in particular does not involve a step of treating a human or animal body using surgery or therapy. In order to distinguish the different data used by the present method, the data are denoted (i.e. referred to) as "XY data" and the like and are defined in terms of the information which they describe, which is then preferably referred to as "XY information" and the like.

The invention also relates to a program which, when running on a computer, causes the computer to perform one or more or all of the method steps described herein and/or to a program storage medium on which the program is stored (in particular in a non-transitory form) and/or to a computer comprising said program storage medium and/or to a (physical, for example electrical, for example technically generated) signal wave, for example a digital signal wave, carrying information which represents the program, for example the aforementioned program, which for example comprises code means which are adapted to perform any or all of the method steps described herein.

The invention also relates to a navigation system for computer-assisted surgery, comprising:
the computer of the preceding claim, for processing the absolute point data and the relative point data;
a detection device for detecting the position of the main and auxiliary points in order to generate the absolute point data and to supply the absolute point data to the computer;
a data interface for receiving the relative point data and for supplying the relative point data to the computer; and
a user interface for receiving data from the computer in order to provide information to the user, wherein the received data are generated by the computer on the basis of the results of the processing performed by the computer.

Within the framework of the invention, computer program elements can be embodied by hardware and/or software (this includes firmware, resident software, micro-code, etc.). Within the framework of the invention, computer program elements can take the form of a computer program product which can be embodied by a computer-usable, for example computer-readable data storage medium comprising computer-usable, for example computer-readable program instructions, "code" or a "computer program" embodied in said data storage medium for use on or in connection with the instruction-executing system. Such a system can be a computer; a computer can be a data processing device comprising means for executing the computer program elements and/or the program in accordance with the invention, for example a data processing device comprising a digital processor (central processing unit or CPU) which executes the computer program elements, and optionally a volatile memory (for example a random access memory or RAM) for storing data used for and/or produced by executing the computer program elements. Within the framework of the present invention, a computer-usable, for example computer-readable data storage medium can be any data storage medium which can include, store, communicate, propagate or transport the program for use on or in connection with the instruction-executing system, apparatus or device. The computer-usable, for example computer-readable data storage medium can for example be, but is not limited to, an electronic, magnetic, optical, electromagnetic, infrared or semiconductor system, apparatus or device or a medium of propagation such as for example the Internet. The computer-usable or computer-readable data storage medium could even for example be paper or another suitable medium onto which the program is printed, since the program could be electronically captured, for example by optically scanning the paper or other suitable medium, and then compiled, interpreted or otherwise processed in a suitable manner. The data storage medium is preferably a non-volatile data storage medium. The computer program product and any software and/or hardware described here form the various means for performing the functions of the invention in the example embodiments. The computer and/or data processing device can for example include a guidance information device which includes means for outputting guidance information. The guidance information can be outputted, for example to a user, visually by a visual indicating means (for example, a monitor and/or a lamp) and/or acoustically by an acoustic indicating means (for example, a loudspeaker and/or a digital speech output device) and/or tactilely by a tactile indicating means (for example, a vibrating element or a vibration element incorporated into an instrument). For the purpose of this document, a computer is a technical computer which for example comprises technical, for example tangible components, for example mechanical and/or electronic components. Any device mentioned as such in this document is a technical and for example tangible device.

It is the function of a marker to be detected by a marker detection device (for example, a camera or an ultrasound receiver or analytical devices such as CT or MRI devices) in such a way that its spatial position (i.e. its spatial location and/or alignment) can be ascertained. The detection device is for example part of a navigation system. The markers can be active markers. An active marker can for example emit electromagnetic radiation and/or waves which can be in the infrared, visible and/or ultraviolet spectral range. A marker can also however be passive, i.e. can for example reflect electromagnetic radiation in the infrared, visible and/or ultraviolet spectral range or can block x-ray radiation. To this end, the marker can be provided with a surface which has corresponding reflective properties or can be made of metal in order to block the x-ray radiation. It is also possible for a marker to reflect and/or emit electromagnetic radiation and/or waves in the radio frequency range or at ultrasound wavelengths. A marker preferably has a spherical and/or spheroid shape and can therefore be referred to as a marker sphere; markers can however also exhibit a cornered, for example cubic, shape.

A marker device can for example be a reference star or a pointer or a single marker or a plurality of (individual) markers which are then preferably in a predetermined spatial relationship. A marker device comprises one, two, three or more markers, wherein two or more such markers are in a predetermined spatial relationship. This predetermined spatial relationship is for example known to a navigation system and is for example stored in a computer of the navigation system.

In another embodiment, a marker device comprises an optical pattern, for example on a two-dimensional surface. The optical pattern might comprise a plurality of geometric shapes like circles, rectangles and/or triangles. The optical pattern can be identified in an image captured by a camera, and the position of the marker device relative to the camera can be determined from the size of the pattern in the image, the orientation of the pattern in the image and the distortion of the pattern in the image. This allows to determine the relative position in up to three rotational dimensions and up to three translational dimensions from a single two-dimensional image.

The position of a marker device can be ascertained, for example by a medical navigation system. If the marker device is attached to an object, such as a bone or a medical instrument, the position of the object can be determined from the position of the marker device and the relative position between the marker device and the object. Determining this relative position is also referred to as registering the marker device and the object. The marker device or the object can be tracked, which means that the position of the marker device or the object is ascertained twice or more over time.

The present invention can be used for any applications which register a patient with image data, such as the AIR app family and TREGS systems of the Applicant.

BRIEF DESCRIPTION OF DRAWINGS

In the following, the invention is described with reference to the enclosed figures which represent preferred embodiments of the invention. The scope of the invention is not however limited to the specific features disclosed in the figures, which show.

DETAILED DESCRIPTION

Figure 1:
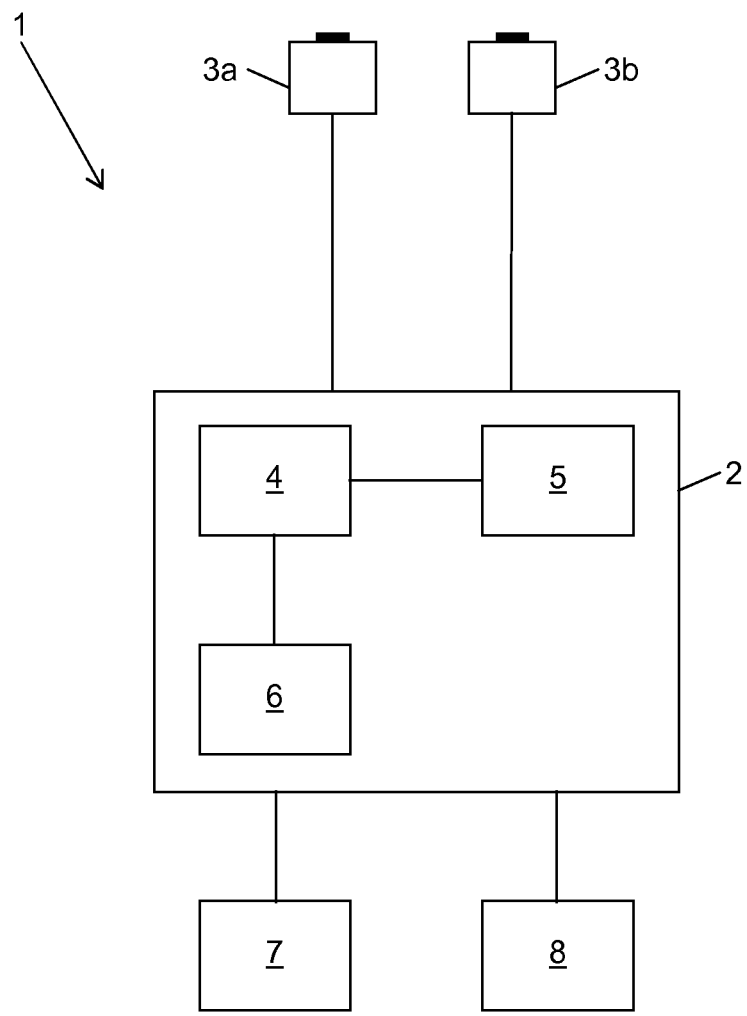
FIG. 1 a system according to the present invention
FIG. 2 two cameras imaging markers on a fabric
FIG. 3 line sets of which the markers lie
FIG. 4 a marker matrix
FIG. 5 a flow chart of an aspect of the invention
FIG. 6 details of the step of the flow chart of FIG. 5
FIG. 7 a first minimal marker set
FIG. 8 a second minimal marker set
FIG. 9 locations of markers in a marker coordinate system
FIG. 10 determination of the marker coordinate system
FIG. 11 an example with five markers in a plane
FIG. 12 a marker configuration in another aspect of the invention
FIG. 13 a flow chart of another aspect of the invention
FIG. 14 a visualization of a test of a marker configuration for flatness.

FIG. 1 shows a system 1 for implementing a method for removing ghost markers for a measured set of medical markers according to the present invention.

The system 1 comprises a computer 2 connected to two cameras 3a and 3b with a known relative position between the two cameras 3a, 3b. The cameras 3a and 3b constitute a stereoscopic camera which captures images which depict medical markers. The location of the medical markers relative to the position of the cameras 3a, 3b can be obtained by image analysis as known in the art. This analysis can be performed in the cameras 3a, 3b, the computer 2 or a combination thereof.

The computer 2 comprises a central processing unit (processor) 4, a memory 5 and an interface 6. Via the interface 6, the computer can be coupled to external devices, such as the cameras 3a, 3b. The processor 4 executes program code in order to perform the methods described herein. The memory 5 stores the program code and/or processed data and/or data to be processed.

The computer 2 is connected to an input device 7, such as a mouse, a keyboard, a touchpad or a touchscreen, and an output device 8, such as a monitor.

Figure 2:
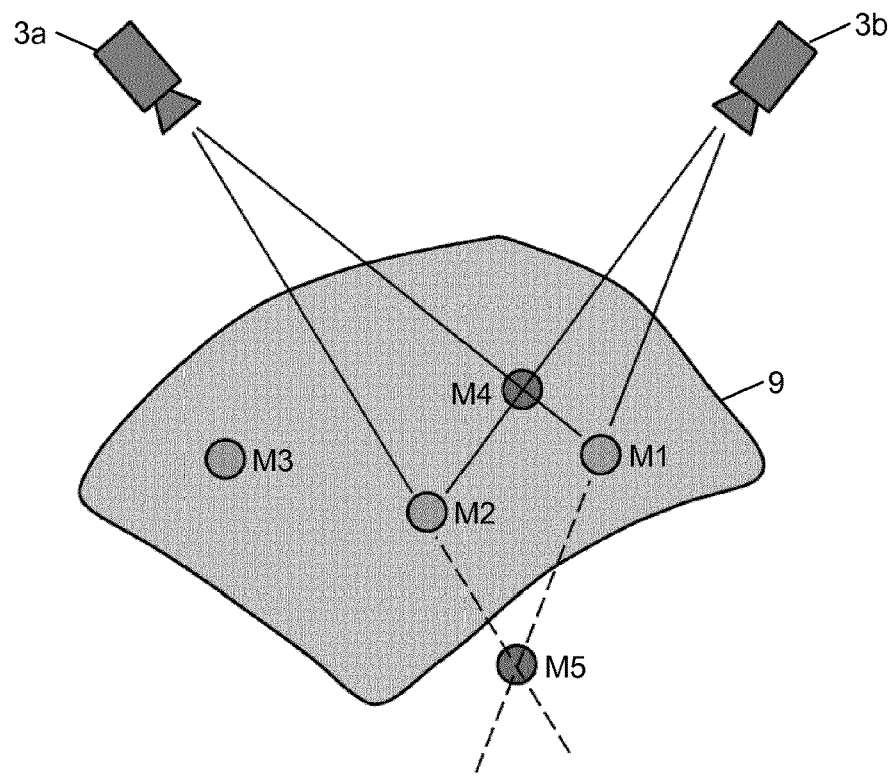

FIG. 2 shows a flexible fabric 9 to which markers M1 to M3 are attached. Since the fabric 9 is flexible, the relative position between the markers M1 to M3 is variable. If a marker detection is performed using the cameras 3a and 3b, not only markers M1 to M3 are detected.

A measured set of medical markers also comprises so-called ghost markers M4 and M5 as explained below.

The principle of detecting markers by use of cameras 3a and 3b is explained with reference to FIG. 3. The light emanating from a marker enters a camera 3a, 3b, typically through its front lens. A lens system of a camera 3a, 3b directs the incoming light onto a two-dimensional image sensor. Depending on the direction of incidence of the incoming light, the light is directed onto a specific pixel of the image detector. This means that every pixel of the detector images all points on a straight line in space corresponding to this pixel. So if an object is imaged at a particular pixel position within the two-dimensional image, the line in space (relative to the camera 3a, 3b) on which the imaged object lies is known.

Figure 3:
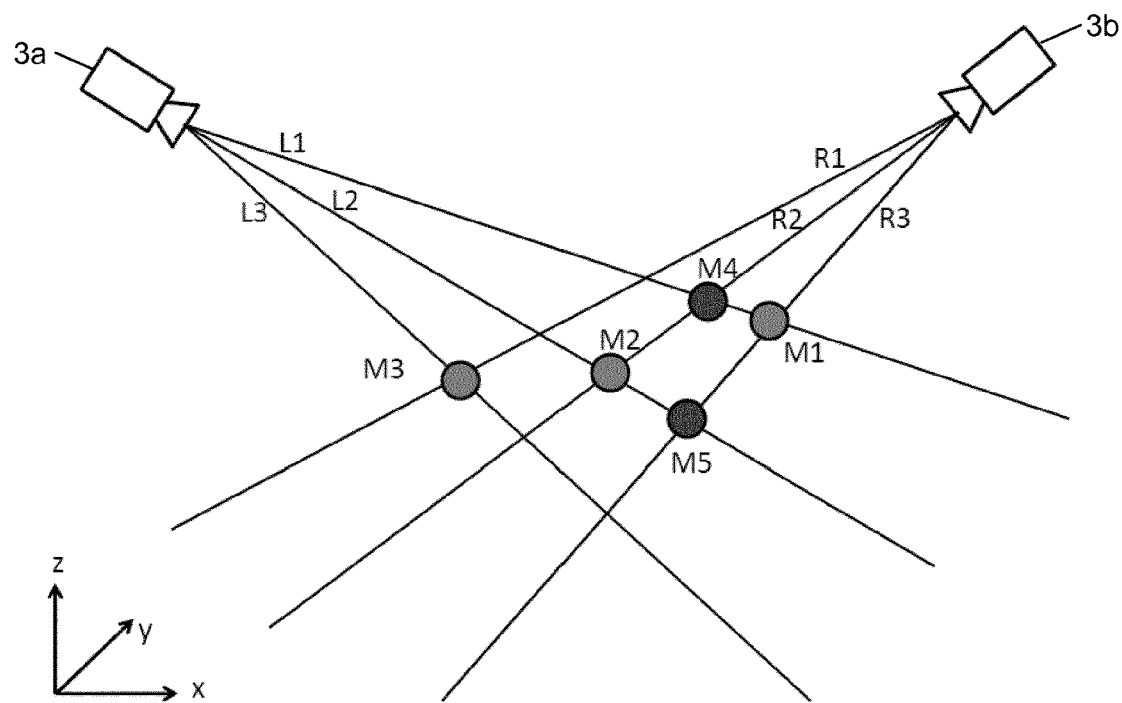

FIG. 3 shows line sets of the cameras 3a, 3b. A first line set comprising lines L1, L2 and L3 belongs to the first camera 3a and a second line set R1, R2, R3 belongs to the second camera 3b. The output image of the camera 3a is analyzed and it is found that there are markers on lines L1, L2 and L3. In analogy, the output image of the camera 3b is analyzed and it is found that there are markers on lines R1, R2 and R3. In the example shown in FIG. 3, the marker M1 lies on lines L1 and R3, marker M2 lies on lines L2 and R2 and marker M3 lies on lines L3 and R1.

The marker M3 can be unambiguously identified at the intersection of lines L3 and R1. However, lines L1, L2, R2 and R3 lie in the same plane. This means that there are not only intersections of lines L2 and R2 at the spatial location of marker M2 and of lines L1 and R3 at the spatial location of marker M1, but there is also an intersection of lines L1 and R2 and an intersection of lines L2 and R3. This means that markers M4 and M5 are detected at the spatial locations of those intersections. Since only markers M1 to M3 are real markers, markers M4 and M5 are referred to as ghost markers. The measured set of medical markers therefore comprises real markers M1 to M3 and ghost markers M4 and M5 and their respective locations in a reference system of the stereoscopic camera. The present invention aims at removing the ghost markers from the measured set of medical markers.

Figure 4:
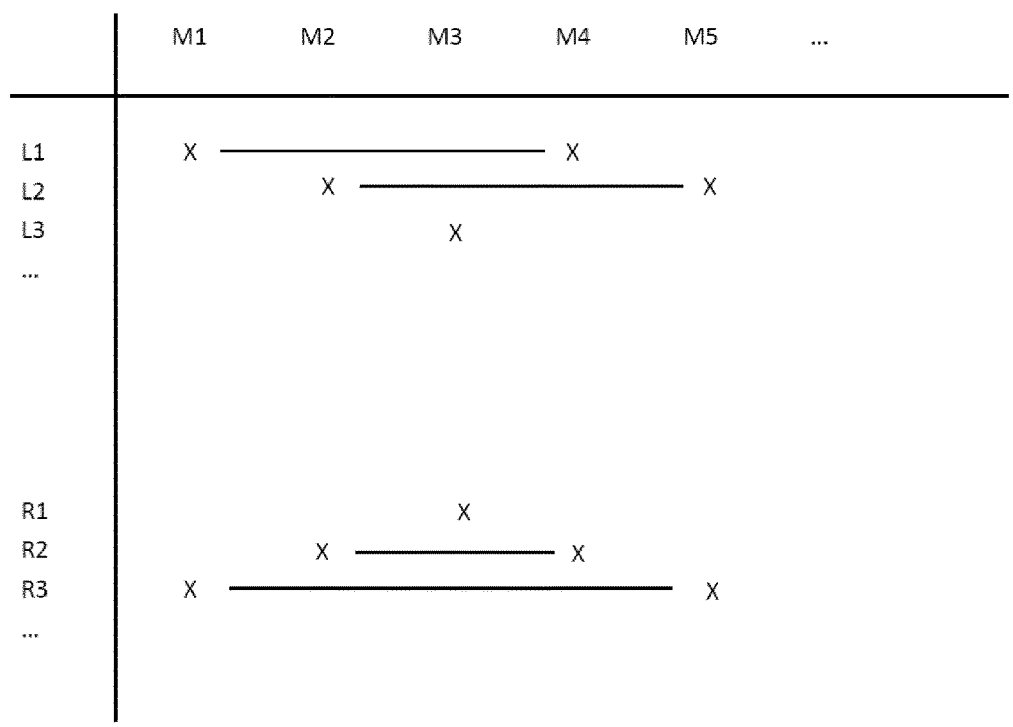

FIG. 4 is an example of a marker matrix output to the computer 2 by the stereoscopic camera. The marker matrix is two-dimensional, with all straight lines of both cameras on which markers are detected in one dimension and all detected markers in the other dimension. For the example shown in FIG. 3, the marker matrix represents the six lines L1 to L3 and R1 to R3 and the five markers M1 to M5. For each of the lines, the marker matrix identifies the markers lying on the respective line, which means that the matrix assigns markers to lines and vice versa. In the example shown in FIG. 4, markers M1 and M4 lie on line L1, markers M2 and M5 lie on line L2, marker M3 lies on line L3, marker M3 lies on line R1, markers M2 and M4 lie on line R2 and markers M1 and M5 lie on line R3.

Figure 5:
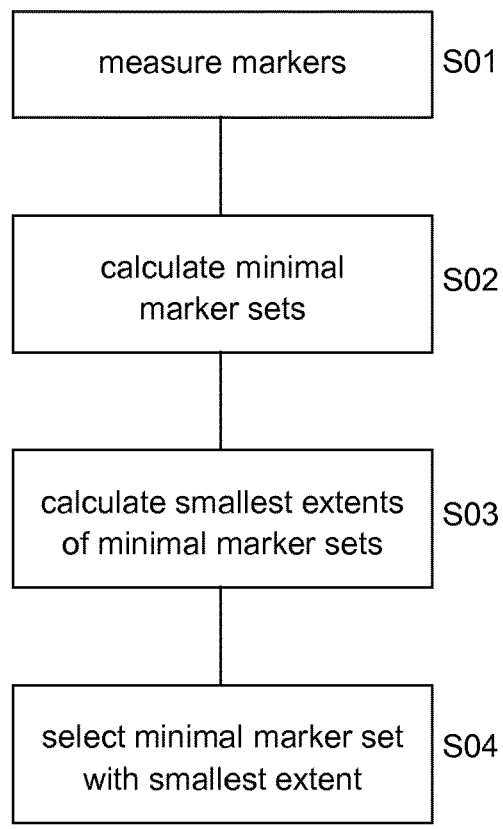

FIG. 5 shows a flowchart of an exemplary aspect of the present invention. In step S01, the markers are measured (or detected). The result of step S01 is the marker matrix as shown in FIG. 4, which is input to the computer 2, together with the locations of the markers in the reference system of the stereoscopic camera.

In step S02, all possible minimal marker sets are calculated from the marker matrix. As can be seen from FIG. 3, the real markers M1 and M2 cause ghost markers M4 and M5. However, if markers M4 and M5 were real markers, they would cause ghost markers M1 and M2 in the measured set of markers.

Step S02 therefore finds all subsets of the measured set which would create ghost markers such that the measured set results. In the present example, a first minimal marker set comprises markers M1, M2 and M3 and a second minimal marker set comprises markers M3, M4 and M5.

Figure 6:
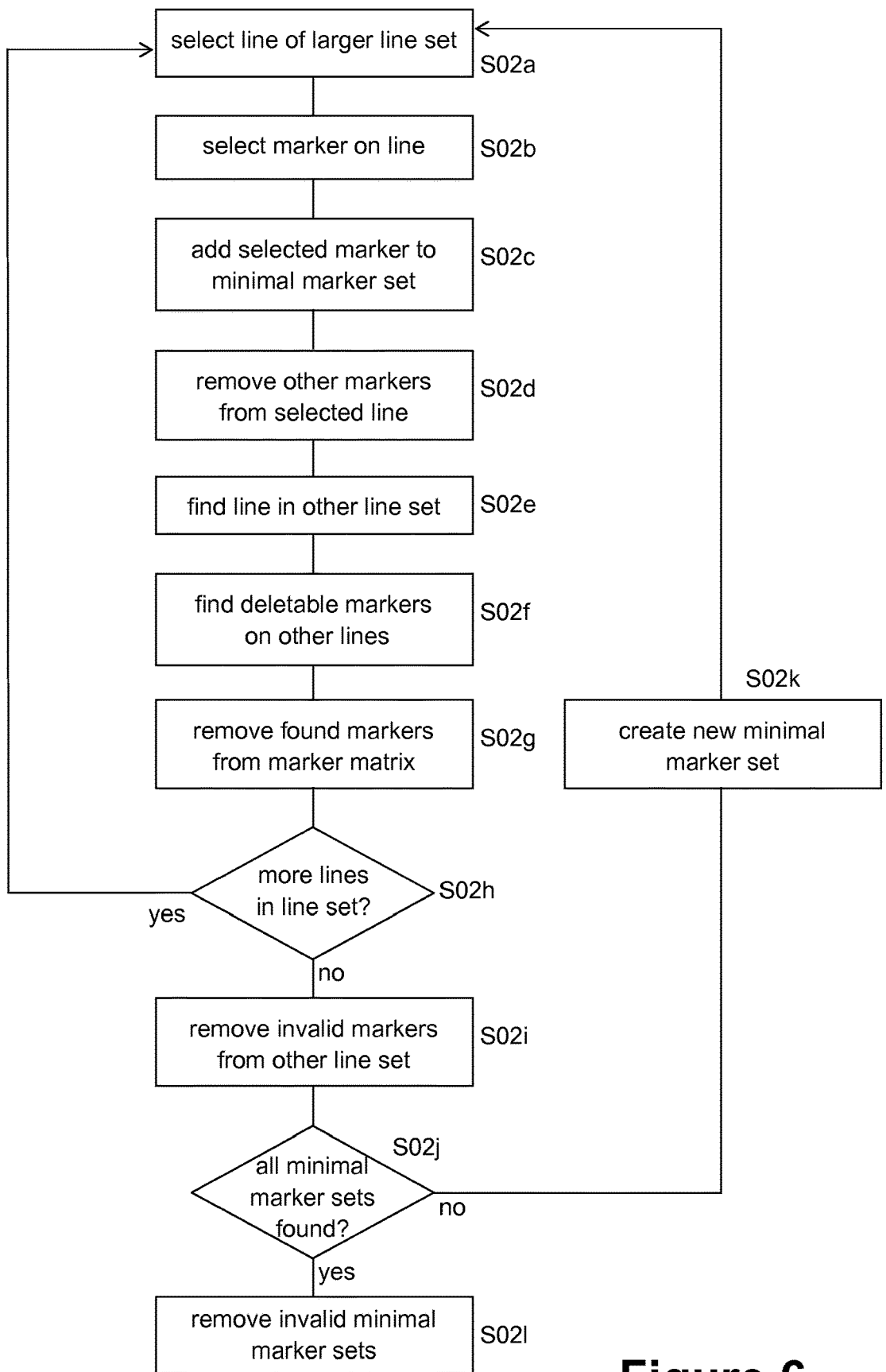

In the present embodiment, a minimal marker set is calculated by iterating through all lines of the larger one of the line sets comprised in the marker matrix. If both line sets comprise the same number of lines, then any one of the two line sets is used as the larger line set. In the following explanation, the process iterates through lines L1 to L3. Details of this process are shown in FIG. 6. In the following explanation, markers and entries in the marker matrix are used synonymously.

It shall be noted that step S02 starts with an empty minimal marker set. Step S02a involves selecting one of the lines, for example line L1. Step S02b involves selecting a marker on the selected line. For example, marker M1 is selected. In step S02c, the selected marker is added to the minimal marker set and the other entries in the selected line are removed in step S02d, thus removing all other markers from this line. In this example, the entry for marker M4 is removed from line L1.

In step S02e, the line of the other line set in the marker matrix to which the selected marker (M1 in the present example) is also assigned is identified. In the present example, this is line R3. Step S02f then involves finding all deletable markers on the other line. A deletable marker is a marker which is not assigned to a line not selected yet (lines L2 and L3 at the present stage of this example) and which is not comprised in the minimal marker set. At the present stage of this example, there is no deletable marker on line R3 because marker M5, which is assigned to line R3, is also assigned to line L2, which was not selected so far. Step S02g then involves removing all entries belonging to the deletable markers found in step S02f from the marker matrix.

Step S02h involves determining whether or not there are more lines to be tested. This is the case (with lines L2 and L3 which have not been selected yet), such that the process returns to step S02a for a new iteration and selects a new line, for example line L2. In step S02b, for example marker M2 on line L2 is selected and added to the minimal marker set in step S02c. The matrix entry for marker M5 is then deleted for line L2 in step S02d. Then line R2 is found in step S02e and marker M4 is identified as a deletable marker in step S02f. Marker M4 is not assigned to a yet unselected line (line L3) and is not comprised in the minimal marker set. The matrix entry for marker M4 in line R4 is then removed in step S02g.

It is then determined step S02h that there is still another line to be analyzed. In the next iteration, line L3 is then selected in step S02a and marker M3 on this line is then selected in step S02b. In step S02c, marker M3 is added to the minimal marker set. It is determined in step S02d that there are no other matrix entries to be removed from line L3. Line R1 is then determined in step S02e, and it is found in step S02f that there are no deletable matrix entries in line R1, such that step S02g does not remove any matrix entries.

Figure 7:
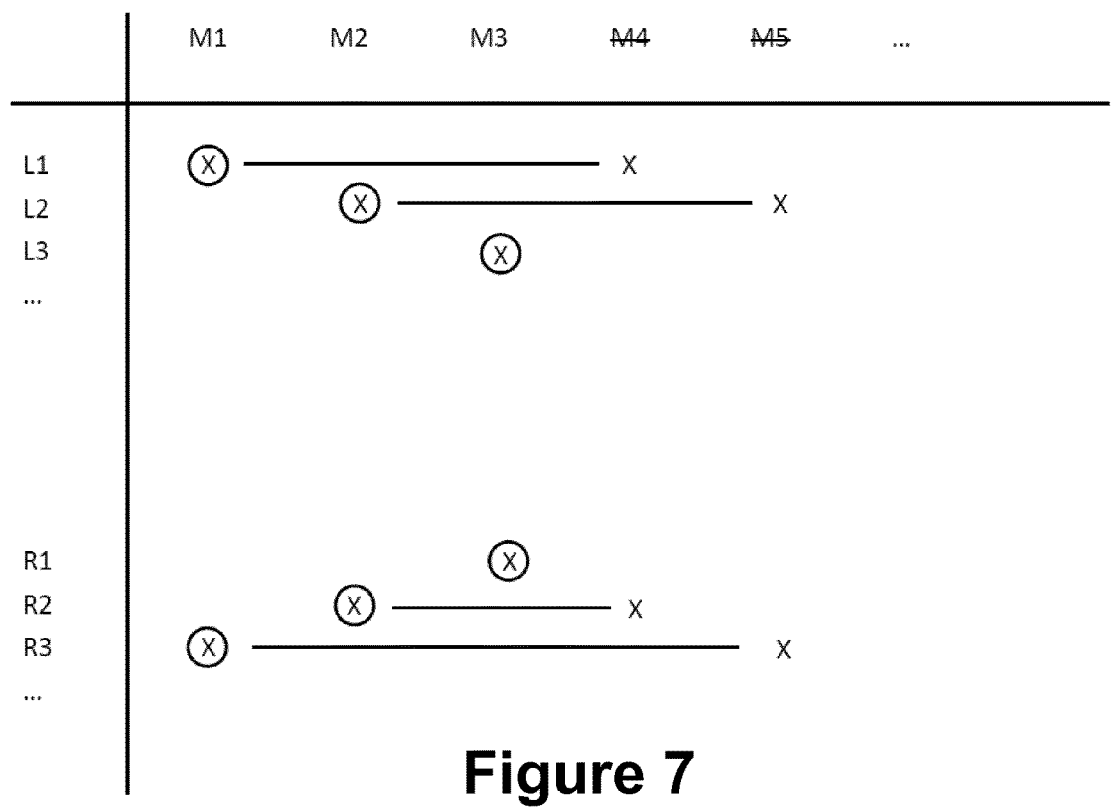

It is then determined in step S02d that there is no more line to be analyzed, such that the process proceeds to step S02i, in which invalid matrix entries are removed. In particular, matrix entries belonging to markers which are not comprised in the minimal marker set are removed. In the present example, those entries assign marker M5 to lines L2 and R3. The result is the marker matrix shown in FIG. 7, wherein entries remaining in the marker matrix are surrounded by circles and all other entries are removed. The resulting marker matrix is also referred to as sub-matrix of the marker matrix. For the result shown in FIG. 7, the minimal marker set comprises markers M1, M2 and M3.

Figure 8:
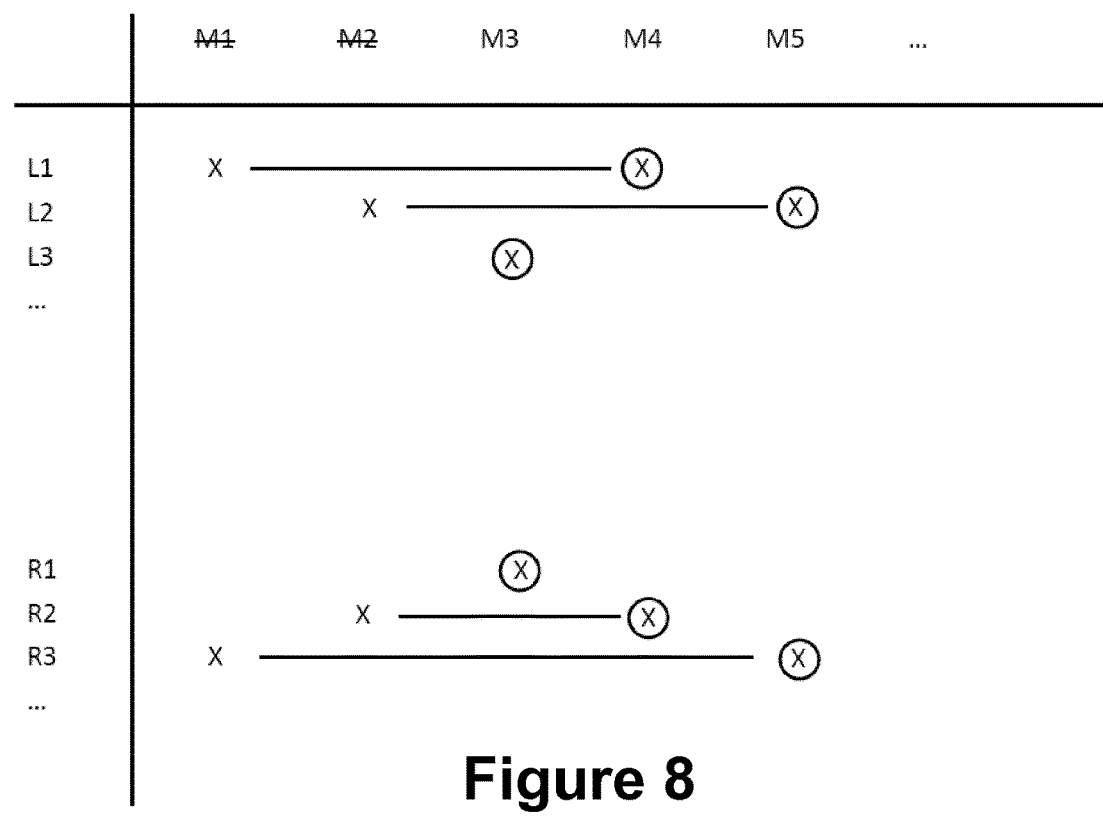

It is then determined in step S02j whether or not all minimal marker sets have been found. This is not the case in the present stage of this example, such that a new, empty minimal marker set is created in step S02k and the process starts again at step S02a, but with the original marker matrix having all measured entries. The process is repeated until all possible permutations of sub-matrices have been found. In the present example, another sub-matrix as shown in FIG. 8 is found. Marker M4 on line L1 is selected in the first iteration. This means that markers M5 and M3 are subsequently added to the minimal marker set.

However, the determined plurality of sub-matrices may also comprise sub-matrices corresponding to invalid minimal marker sets. A minimal marker set is invalid if the corresponding sub-matrix comprises at least one line to which no marker is assigned. As can be seen from the example in FIG. 3, the combination of markers M1, M5 and M3 cannot be a minimal marker set, because no marker would be detected on line R2 and no ghost markers can occur. The invalid minimal marker sets are therefore deleted in step S02l.

Instead of removing invalid minimal marker sets, it is possible to avoid the creation of invalid minimal marker sets. For example, the selection of a marker in step S02b can be amended appropriately.

Step S03 of FIG. 5 then involves calculating the smallest extent of each minimal marker set, wherein the smallest extent is the smallest extent among the extents in three orthogonal directions. The markers in the minimal marker set occupy a volume having a particular size, and the size is defined along the three orthogonal directions.

If the arrangement of real markers is considered to be flat, then the real markers basically lie in a plane. However, due to the nature of the intersecting lines in space, the detected ghost markers do not lie in this plane. It can therefore be assumed that the "flattest" out of the possible minimal marker sets only comprises real markers and no ghost markers.

Figure 9:
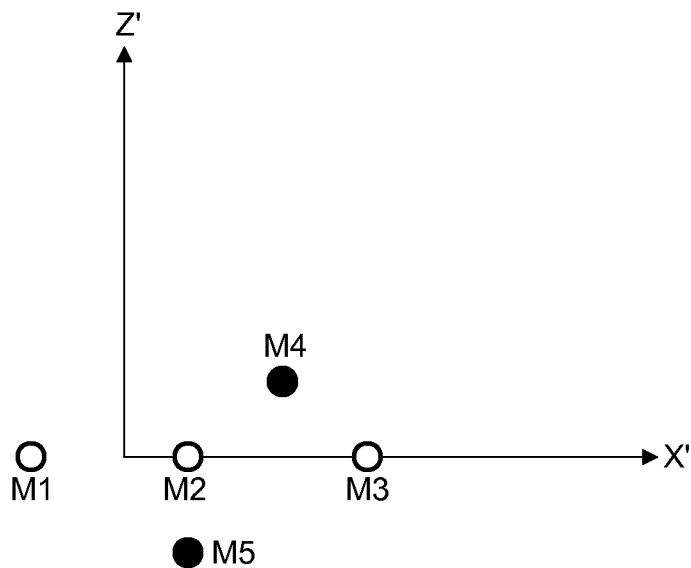

This can be seen from FIG. 9. It shows a lateral view onto the markers in the measured set. Markers M1, M2 and M3 lie in the X'-Y'-plane of a marker reference system, while ghost markers M4 and M5 stick out in the Z'-direction.

The geometric size of a minimal marker set means the size of a space occupied by the markers in the minimal marker set. This size is defined in the three orthogonal directions. It is necessary to find those three orthogonal directions such that the smallest of the three extents along those three directions is minimized. This can be achieved by a statistical analysis of the minimal marker set in terms of finding the principal axes.

Figure 10:
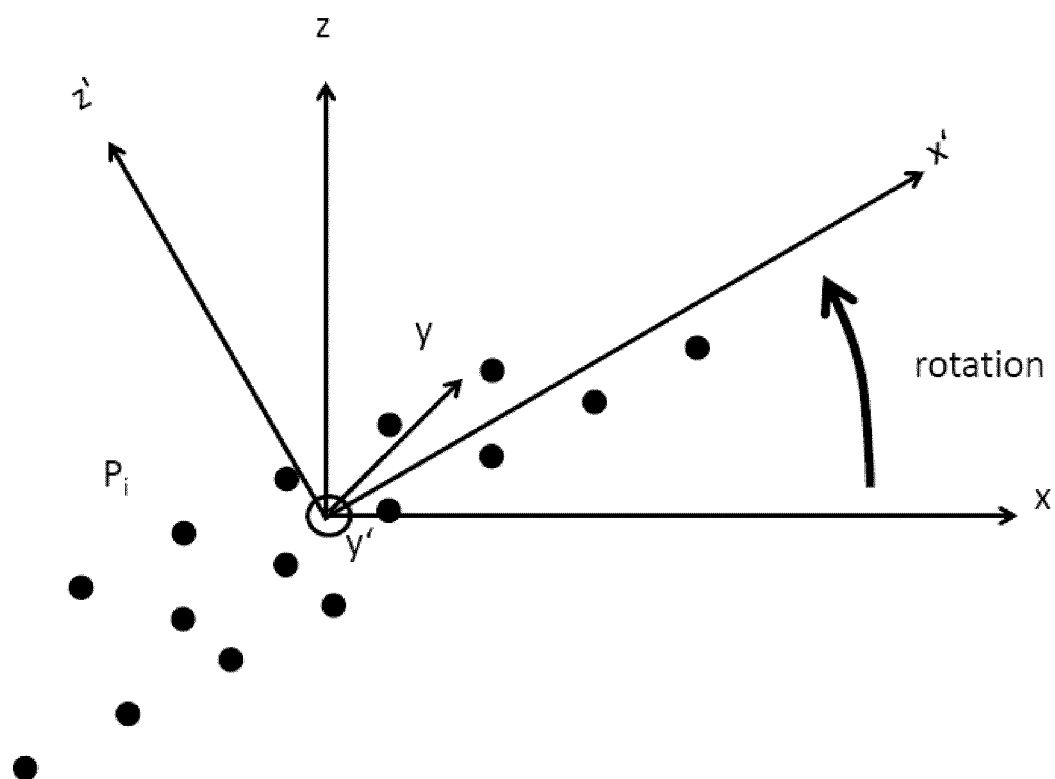

In one implementation, the three orthogonal directions define the axes of the marker reference system, which is a coordinate system aligned with the markers in the minimal marker set such that the extent of the volume occupied by the markers in one of the axes of the coordinate system is minimized. The camera coordinate system is shifted into the center of the markers comprised in the minimal marker set. Then a covariance matrix of the locations of the markers of the minimal marker set in the marker reference system is created. The eigenvectors of the covariance matrix are calculated next. Those eigenvectors constitute a transformed reference system, which is the marker reference system. This is shown in FIG. 10, but with a larger minimal marker set for better visibility. The camera reference system formed by orthogonal axes X, Y and Z is transformed into the marker reference system formed by axes X', Y' and Z' having the directions of the eigenvectors of the covariance matrix. The extents of the minimal marker set in the directions of the three axes of the marker reference system are calculated and the smallest of those three extents is selected as the smallest extent of the minimal marker set. This is repeated for all minimal marker sets.

Step S04 then involves selecting the minimal marker set having the smallest out of the smallest extents. This selected minimal marker set is the flattest of all possible minimal marker sets and is therefore considered as a ghost marker free marker set.

Figure 11:
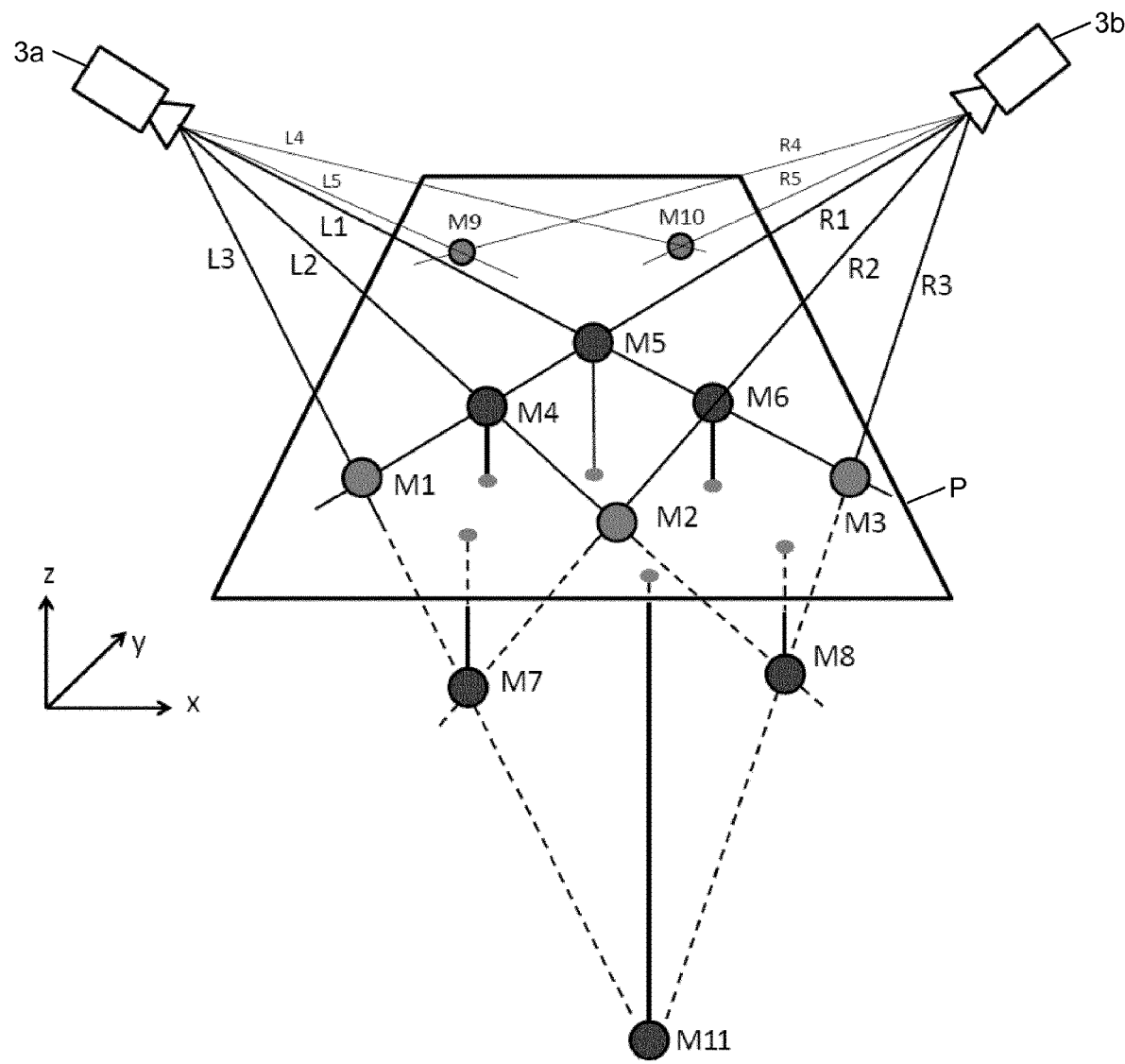

The justification for selecting the flattest of the possible minimal marker sets is explained with reference to FIG. 11. This figure shows five real markers M1, M2, M3, M9 and M10 arranged in a plane P. If those markers are measured using cameras 3a and 3b, also ghost markers M4, M5, M6, M7, M8 and M9 occur in the measured set. As can be seen from FIG. 11, those ghost markers do not lie in the plane P, but spaced apart therefrom. Markers M9 and M10 are always comprised in the minimal marker set. Due to the distances of the ghost markers to the plane P, the only minimal marker set which is flat or almost flat is the minimal marker set comprising markers M1, M2, M3, M9 and M10, and thus the real markers.

The pseudocode listed above will now be explained with reference to the marker configuration of FIG. 3 and the marker matrix of FIG. 4.

ActiveRowsLeft and ActiveRowsRight each have the value 3 and MarkerSize is 5. MarkerSizeLimit is thus 31 and therefore has 5 bits. MarkerMask in loop1 then counts from 1 to 31. In the present example, the most significant bit of a variable represents marker M1 and the least significant bit represents marker M5.

For values of MarkerMask between 1 and 6, the binary representation has less than three bits set, such that loop1 is left in step 9. For MarkerMask=7, the binary representation is 00111 and thus has three bits set.

In steps 10 and 11, MarkersFoundLeft and MarkersFoundRight are each set to 0 (binary 00000), and starting in line 12, loop2 counts from 1 to 3.

Markers M1 and M4 lie on line L1 and marker M3 lies on line R1. For LineNumber=1, LeftCameraRow is therefore 10010 and RightCameraRow is therefore 00100. This means that LeftCameraRowResult becomes 00010 in step 15 and RightCameraRowResult becomes 00100 in step 19. In both variables, no more than 1 bit is set, such that the process continues with step 22. In this step, the OR combination changes MarkersFoundLeft from 00000 to 00010. In analogy, step 23 changes MarkersFoundRight from 00000 to 00100.

loop2 is then repeated with LineNumber=2. LeftCameraRow is then 01001 and Right CameraRow is 01010. LeftCameraRowResult then becomes 00001 and RightCameraRowResult becomes 00010. MarkersFoundLeft then changes from 00010 to 00011 and MarkersFoundRight changes from 00100 to 00110.

loop2 is then repeated with LineNumber=3. LeftCameraRow is then 00100 and Right CameraRow is 10001. LeftCameraRowResult then becomes 00100 and RightCameraRowResult becomes 00001. MarkersFoundLeft then changes from 00011 to 00111 and MarkersFoundRight changes from 00110 to 00111.

The AND combination of MarkersFoundLeft and MarkersFoundRight in step 25 then results in MarkersFound=00111. In this variable, three bits corresponding to three markers M3, M4 and M5 are set, which equals the number of lines in the two line sets. The set of M3, M4 and M5 is therefore found as a minimal marker set.

loop1 is then repeated for the next values of MarkerMask. Details are now explained for MarkerMask=14, which is binary 01110.

MarkersFoundLeft and MarkersFoundRight are each set to 00000 in steps 10 and 11. loop2 counts LineNumber from 1 to 3.

For LineNumer=1, LeftCameraRow is 10010 and RightCameraRow is 00100.

LeftCameraRowResult becomes 00010 and RightCameraRowResult becomes 00100. MarkersFoundLeft changes from 00000 to 00010 and MarkersFoundRight from 00000 to 00100.

For LineNumer=2, LeftCameraRow is 01001 and RightCameraRow is 01010. LeftCameraRowResult becomes 01000 and RightCameraRowResult becomes 01010. RightCameraRowResult this has two bits set, such that loop2 is quit in step 21 and loop1 continues with MarkerMask=14. As a result, the set of markers M2, M3 and M4 represented by MarkerMask=14 is not a minimal marker set, because it has two markers in line R2.

The code then identifies marker sets represented by MarkerMask from 15 to 27 as not being minimal marker sets.

For MarkerMask=28, the binary representation is 11100. In steps 10 and 11, MarkersFoundLeft and MarkersFoundRight are thus each set to 0 (binary 00000), and starting in line 12, loop2 counts from 1 to 3.

For LineNumer=1, LeftCameraRow is 10010 and RightCameraRow is 00100. LeftCameraRowResult becomes 10000 and RightCameraRowResult becomes 00100. MarkersFoundLeft changes from 00000 to 10000 and MarkersFoundRight from 00000 to 00100.

For LineNumer=2, LeftCameraRow is 01001 and RightCameraRow is 01010. LeftCameraRowResult becomes 01000 and RightCameraRowResult becomes 01000. MarkersFoundLeft changes from 10000 to 11000 and MarkersFoundRight from 00100 to 01100.

For LineNumer=3, LeftCameraRow is 00100 and RightCameraRow is 10001. LeftCameraRowResult becomes 00100 and RightCameraRowResult becomes 10000. MarkersFoundLeft changes from 11000 to 11100 and MarkersFoundRight from 01100 to 11100.

The AND combination of MarkersFoundLeft and MarkersFoundRight in step 25 then results in MarkersFound=11100. In this variable, three bits corresponding to three markers M3, M4 and M5 are set, which equals the number of lines in the two line sets. The set of M1, M2 and M3 is therefore found as a minimal marker set.

The further iterations of loop1 for MarkerMask from 29 to 31 does not find any further minimal marker sets, such that the identified minimal marker sets are M1, M2, M3 and M3, M4, M5.

Figure 12:
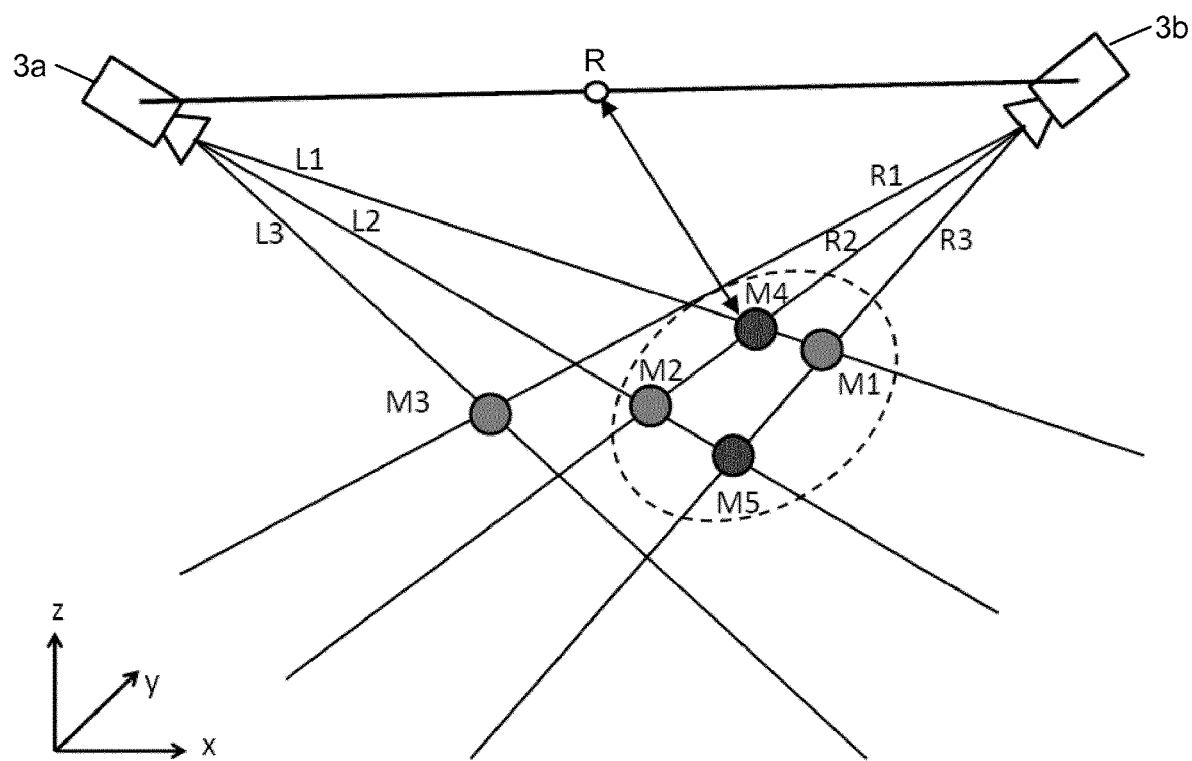

FIG. 12 shows another aspect of the present invention. It shows the marker constellation of markers M1, M2 and M3 and the ghost markers M4 and M5 of FIG. 3. In addition, it shows a reference point R of the stereoscopic camera. In the present case, this reference point is the center of the line between the cameras $3a$ and $3b$.

Figure 13:
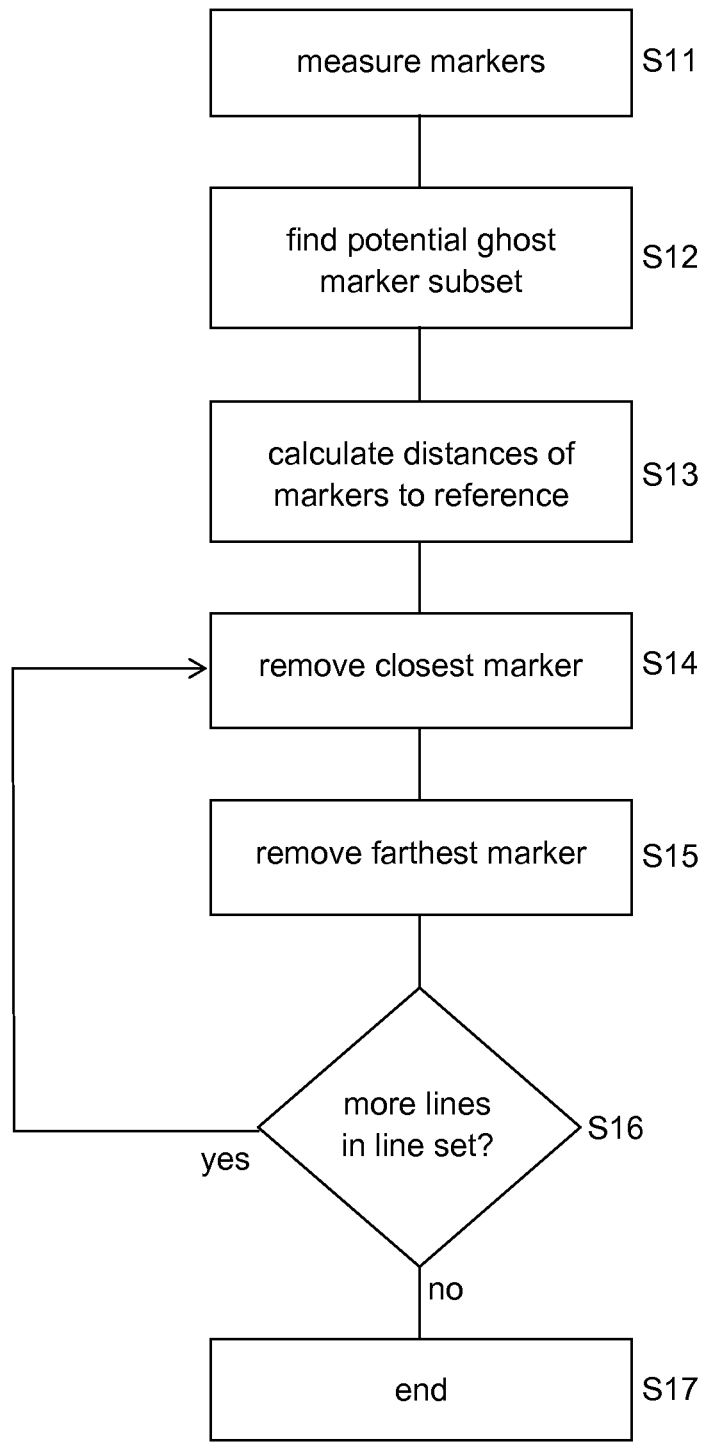

FIG. 13 shows a flow chart of the method according to the second aspect of the present invention.

Step S11 involves measuring the medical markers, thus resulting in a measured set of markers comprising markers M1 to M5, that is real markers M1 to M3 and ghost markers M4 and M5, together with the locations of all those markers in a camera reference system. The measured set of medical markers can be represented by a marker matrix as shown in and explained with reference to FIG. 4.

Step S12 involves finding a potential ghost marker subset of the measured set of medical markers. The potential ghost marker subset only comprises real markers which can have caused ghost markers and those ghost markers. In the example shown in FIG. 12, the potential ghost marker subset comprises markers M1, M2, M4 and M5.

Using a marker matrix, which is output by the stereoscopic camera, as shown in FIG. 4, the markers to be added to the potential ghost marker subset can be identified by finding all lines which have assigned thereto more than one marker and adding the markers assigned to those lines to the potential ghost marker subset.

In an optional step subsequent to step S12, the potential ghost marker subset is pruned. This means that only markers in the potential ghost marker subset which lie in the same plane remain in the potential ghost marker subset and all other markers are removed therefrom. This is motivated by the fact that the constellation in which two lines corresponding to the first camera and two lines corresponding to the second camera all lie in a first plane causes ghost markers in the first plane, and two lines corresponding to the first camera and two lines corresponding to the second camera lying in a second plane cause ghost markers in the second plane.

In the subsequent steps of this embodiment, only ghost markers in a particular plane are considered. If there are ghost markers in different planes, different potential ghost marker subsets are created and processed iteratively.

Step S13 involves calculating the distances of all markers in the potential ghost marker subset to the reference point R. It is of course also possible to not calculate the distances for a particular potential ghost marker subset, but once for all potential ghost markers in the measured set of medical markers and to retrieve the distances for the markers comprised in the potential ghost marker subset.

Step S14 involves removing the marker having the smallest distance to the reference R from the potential ghost marker subset and the measured set. Step S15 then involves removing the marker having the largest distance to the reference R from the potential ghost marker subset and the measured set. In the example shown in FIG. 12, markers M4 and M5 are removed from the potential ghost marker subset and the measured set. This means that markers M1, M2 and M3 remain in the measured set.

Step S16 involves determining whether or not there are more ghost markers in the potential ghost marker subset. If this is the case, the process returns to step S14 and removes the markers which are now the closest and the farthest from the reference R from the potential ghost marker subset and the measured set. If there are no more ghost markers in the potential ghost marker subset, the process ends at step S17.

In one example, the number of ghost markers in the initial potential ghost marker subset found in step S12 is determined. The number of markers in the potential ghost marker subset is the product of the number of lines of the first line set and the number of lines in the second line set which lie in the same plane. The minimal number of real markers which could cause the potential ghost marker subset equals the larger one of the number of lines of the first line set and the number of lines of the second line set lying in this plane. In the example shown in FIG. 12, two lines L1 and L2 of camera $3a$ and two lines R2 and R3 corresponding to the camera $3b$ lie in the same plane, which means that the potential ghost marker subset comprises four markers (M1, M2, M4 and M5) which can be caused by two real markers. The potential ghost marker subset therefore comprises two ghost markers.

If there is an odd number of ghost markers in the initial potential ghost marker subset, there are two options. In the first option, one of the steps S14 and S15 is skipped in the last iteration of the method. For example, the average distance of all remaining markers in the potential ghost marker subset or all remaining markers in the potential ghost marker subset without the markers having the smallest and the largest distance to the reference R is calculated and the one of the closest and the farthest markers in the potential ghost marker subset having the larger difference to this average is removed from the potential ghost marker subset. In the second option, both steps S14 and S15 are performed anyway. This means that a real marker is removed from the measured set, but at the same time, all ghost markers are reliably removed.

As explained above, the present invention works best if the constellation of the real markers is basically flat, which means that it widely extends over a two-dimensional area, but hardly in a direction perpendicular thereto. One potential test whether or not this situation is given is explained with reference to FIG. 14.

Figure 14:
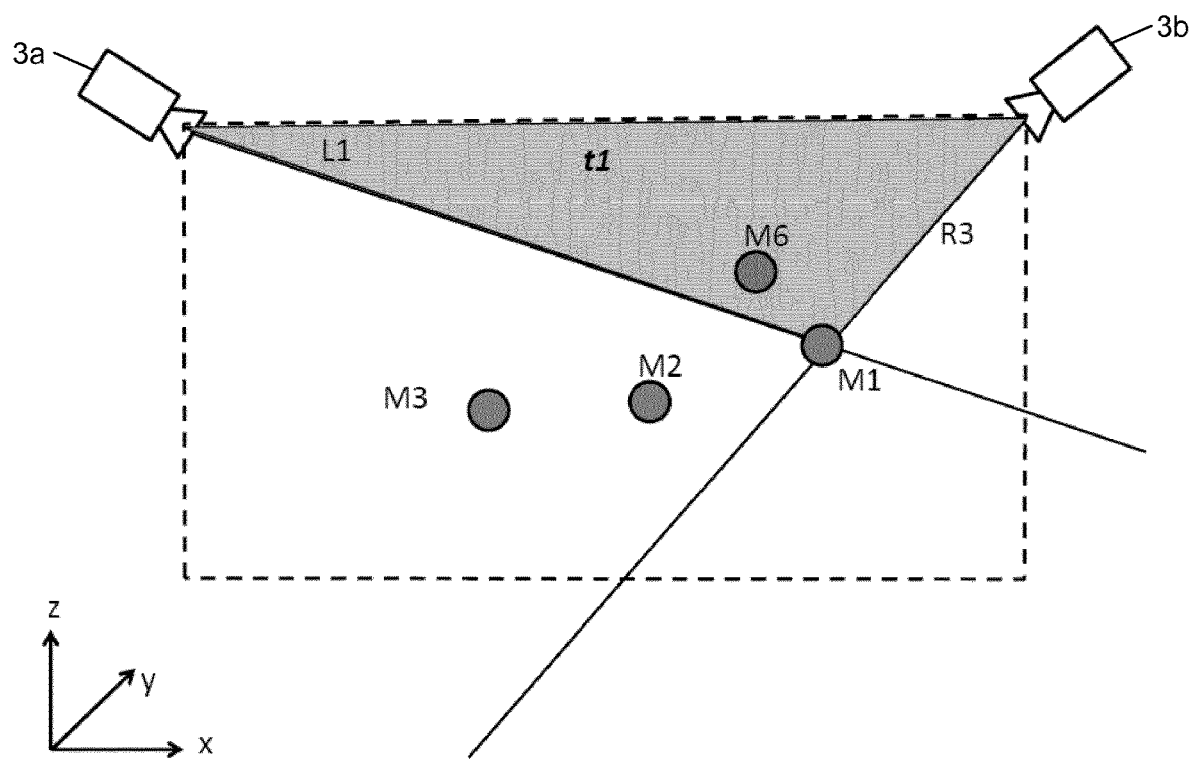

In FIG. 14, there are real markers M1, M2, M3 and M6. For each of those markers, the triangle between the respective marker, the first camera $3a$ and the second camera $3b$ is calculated. If another marker lies within this triangle, the marker arrangement is considered as not being flat. In the present case, marker M6 lies in the triangle corresponding to marker M1. The marker arrangement is therefore not considered to be flat or near-flat.

The invention claimed is:

1. A method for removing ghost markers from a measured set of medical markers, wherein the measured set of markers represents the positions of real markers and the positions of ghost markers, comprising the steps of:

measuring the set of medical markers with a first and a second camera;

calculating all possible minimal marker sets, wherein
each of the calculated minimal marker sets:
is a subset of the measured set, and
consists of the smallest possible number of markers
which would cause the measured set to be measured;
calculating the smallest extent of each minimal marker
set, wherein the smallest extent is the smallest extent
among the extents in three orthogonal directions; and
selecting the minimal marker set having the smallest
extent out of the smallest extents as a marker set
without ghost markers.

2. The method of claim 1, wherein the three orthogonal directions are set such that the smallest extent of a minimal marker set is minimized.

3. The method of claim 1, wherein the step of calculating the smallest extent involves calculating the principal axes of the minimal marker set and using the directions of the principal axes as the three orthogonal directions.

4. The method of claim 3, wherein the principal axes correspond to eigenvectors of a covariance matrix of the positions of the markers in the measured set in a measurement coordinate system.

5. The method of claim 4, wherein the eigenvalues of the covariance matrix are calculated and the smallest extent is calculated on the basis of at least one of the eigenvalues.

6. The method of claim 5, wherein the smallest eigenvalue of each minimal marker set is used as the smallest extent of the minimal marker set.

7. The method of claim 5, wherein the product of the eigenvalues is calculated for each minimal marker set and this product is used as the smallest extent.

8. The method of claim 1, wherein the measured set of medical markers is measured using two cameras and calculating the minimal marker sets involves the steps of:
acquiring a first line set for the first camera and a second line set for the second camera, wherein each line set consists of a set of straight lines in space, each straight line runs through the front lens of the corresponding camera and at least one real marker lies on a straight line;
finding a ghost marker susceptible line set, wherein a ghost marker susceptible line set comprises all lines of the first and second line sets which lie in the same plane and each of those lines intersects at least two lines of the respective other line set in the ghost marker susceptible line set, and comprises at least two lines of each line set;
determining the minimal marker sets as those marker sets for which each line of the line set having more of its lines in the ghost marker susceptible line set intersects exactly one line of the other line set and there is at least one marker on each line of the other line set.

9. The method of claim 1, wherein the measured set of medical markers is measured using a stereoscopic camera comprising two cameras and calculating the minimal marker sets involves the steps of:
acquiring, from the stereoscopic camera, a marker matrix assigning each marker in the measured set to one line in a first line set for the first camera and to one line in a second line set for the second camera, wherein each line set consists of a set of straight lines in space, each straight line runs through the front lens of the corresponding camera and at least one real marker lies on a straight line;
finding all sub-matrices of the marker matrix in which every line of the larger one of the two line sets has exactly one marker assigned thereto and the lines of the other line set only have markers assigned thereto which correspond to the markers assigned to the lines in the larger line set;
determining the minimal marker sets from the sub-matrices.

10. The method of claim 1, wherein the measured set of medical markers is measured using a stereoscopic camera comprising two cameras and calculating the minimal marker sets involves the steps of:
acquiring, from the stereoscopic camera, a marker matrix assigning each marker in the measured set to one line in a first line set for the first camera and to one line in a second line set for the second camera, wherein each line set consists of a set of straight lines in space, each straight line runs through the front lens of the corresponding camera and at least one real marker lies on a straight line;
finding all sub-matrices of the marker matrix in which every line of the first line set and every line of the second line set has exactly one marker assigned thereto and every marker in the sub-matrix is assigned to exactly one line of the first line set and to exactly one line of the second line set; and
determining the minimal marker sets from the sub-matrices.

11. A method for removing ghost markers from a measured set of medical markers, wherein the set of measured markers represents the positions of real markers and the positions of ghost markers and was obtained by use of a stereoscopic camera comprising two cameras, comprising the steps of:
finding a potential ghost marker subset of the measured set, the potential ghost marker subset comprising real markers and ghost markers caused by the real markers;
calculating the distance of each marker in the potential ghost marker subset to the stereoscopic camera;
removing the marker with the smallest distance and the marker with the largest distance from the measured set and the potential ghost marker subset;
repeating the removing step if the potential ghost marker subset comprises further potential ghost markers.

12. The method of claim 11, wherein the distance between a marker and the stereoscopic camera is the distance between the marker and the middle of a straight line which connects the two cameras.

13. The method of claim 12, wherein the step of finding a potential ghost marker subset involves the steps of:
acquiring a first line set for the first camera and a second line set for the second camera, wherein each line set consists of a set of straight lines in space, each straight line runs through the front lens of the corresponding camera and at least one real marker lies on a straight line;
finding a ghost marker susceptible line set, wherein a ghost marker susceptible line set comprises all lines of the first and second line sets which lie in the same plane and each of those lines intersects at least two lines of the respective other line set in the ghost marker susceptible line set, and comprises at least two lines of each line set;
adding all markers of the measured set to the potential ghost marker subset that lie on an intersection of two lines of the ghost marker susceptible line set.

14. At least one non-transitory computer-readable medium comprising instructions that, in response to execution of the instructions by one or more processors, cause the one or more processors to perform the following operations to remove ghost markers from a measured set of medical markers, wherein the measured set of markers represents the positions of real markers and the positions of ghost markers:
    measure the set of medical markers with a first and a second camera;
    calculating all possible minimal marker sets, wherein each of the calculated minimal marker sets:
        is a subset of the measured set, and
        consists of the smallest possible number of markers which would cause the measured set to be measured;
    calculate the smallest extent of each minimal marker set, wherein the smallest extent is the smallest extent among the extents in three orthogonal directions; and
    select the minimal marker set having the smallest extent out of the smallest extents as a marker set without ghost markers.

15. A system to remove ghost markers from a measured set of medical markers, wherein the measured set of markers represents the positions of real markers and the positions of ghost markers:
    at least one computer having at least one processor and associated memory;
    a first and a second camera operably connected to the at least one computer;
    computer instructions stored in the associated memory, which when executed by the at least one processor, cause the at least one processor to:
        measure the set of medical markers with the first and a second camera;
        calculate all possible minimal marker sets, wherein each of the calculated minimal marker sets:
            is a subset of the measured set, and
            consists of the smallest possible number of markers which would cause the measured set to be measured;
        calculate the smallest extent of each minimal marker set, wherein the smallest extent is the smallest extent among the extents in three orthogonal directions; and
        select the minimal marker set having the smallest extent out of the smallest extents as a marker set without ghost markers.

\* \* \* \* \*